United States Patent [19]

Honganen et al.

[11] Patent Number: 4,797,207
[45] Date of Patent: Jan. 10, 1989

[54] APPARATUS FOR CONTROLLING A PUMP TO ACCOUNT FOR COMPRESSIBILITY OF LIQUIDS IN OBTAINING STEADY FLOW

[75] Inventors: Ronald E. Honganen, Campbell; Robert L. Howe, San Ramon; Leslie A. Miller, San Jose, all of Calif.

[73] Assignee: Spectra Physics, Inc., San Jose, Calif.

[21] Appl. No.: 913,356

[22] Filed: Sep. 30, 1986

[51] Int. Cl.⁴ .......................................... B01D 15/08
[52] U.S. Cl. ................................. 210/198.2; 210/85; 210/101; 417/18; 417/265
[58] Field of Search ................ 210/656, 659, 101, 85, 210/198.2; 417/18, 53, 265

[56] References Cited

U.S. PATENT DOCUMENTS

| | | | |
|---|---|---|---|
| 4,128,476 | 12/1978 | Rock | 210/101 |
| 4,137,011 | 1/1979 | Rock | 417/22 |
| 4,310,420 | 1/1982 | Konishi | 210/101 |
| 4,347,131 | 8/1982 | Brownlee | 210/101 |
| 4,352,636 | 10/1982 | Patterson | 417/53 |
| 4,422,942 | 12/1983 | Allington | 210/101 |
| 4,478,713 | 10/1984 | Girot | 210/101 |
| 4,552,513 | 11/1985 | Miller | 417/18 |
| 4,595,495 | 6/1986 | Yotam | 210/198.2 |
| 4,595,496 | 6/1986 | Carson | 210/101 |

*Primary Examiner*—Ernest G. Therkorn
*Attorney, Agent, or Firm*—Ciotti & Murashige, Irell & Manella

[57] ABSTRACT

There is disclosed herein an apparatus and method for controlling a dual piston pump for a liquid chromatography system so as to pump a flow of solvent through the liquid chromatography column at a constant flow rate and with a solvent composition which is substantially equal to the desired solvent composition despite changing conditions of compressibility of the solvent. The control system uses a computer which measures the time it takes the pump shaft to move through an overlap region in the pump cycle when both pistons are simultaneously pumping as normalized to the time taken by the pump to move through a constant velocity portion of the piston travel defined by the user. This time is compared to the time stored in the computer for the particular flow rate used to measure the time defined above for the pump to move through the overlap region for an incompressible solvent at low pressure as normalized to the time taken by the input piston to move through the same user defined segment of the constant velocity portion of the travel of the input piston. The ratio of these two times is then used in an algorithm to derive a correction factor for compressibility. This correction factor is then used to control the flow rate and the makeup of the solvent composition to maintain the correct values over changing conditions of solvent compressibility.

9 Claims, 5 Drawing Sheets $$CF = Z - \frac{Z}{\left(\dfrac{T_{DF}}{T_{LF}} - 1\right)} \cdot \left[\frac{T_{MDF}}{T_{MLF}} - 1\right]$$

$\phantom{CF = Z - }\phantom{\dfrac{Z}{\left(\dfrac{T_{DF}}{T_{LF}} - 1\right)}}$ 82 $\phantom{\cdot\left[\dfrac{T_{MDF}}{T_{MLF}}\right]}$ 80

WHERE

CF = CORRECTION FACTOR

Z = CONSTANT EQUAL TO % OF PUMP STROKE VOLUME OF PISTON 39 IN THE OVERLAP OR DOUBLE FLOW REGION WHICH IS AVAILABLE FOR COMPRESSION AND DECOMPRESSION OF A SOLVENT TO MAINTAIN A CONSTANT FLOW RATE.

$T_{DF}$ = TIME FOR PUMP SHAFT TO ROTATE THROUGH THE OVERLAP ANGLE WITH INCOMPRESSIBLE SOLVENT AND CONSTANT PRESSURE AND CONSTANT FLOW RATE.

$T_{LF}$ = TIME WITH INCOMPRESSIBLE SOLVENT FOR PUMP SHAFT TO ROTATE THROUGH A DEFINED PORTION IN THE CONSTANT VELOCITY, LINEAR FLOW REGION UNDER THE SAME CONDITIONS AS $T_{DF}$ REGARDING PRESSURE AND FLOW RATE.

$T_{MDF}$ = MEASURED TIME FOR PUMP SHAFT TO ROTATE THROUGH THE OVERLAP ANGLE WITH A COMPRESSIBLE SOLVENT AT A CONSTANT FLOW RATE.

$T_{MLF}$ = MEASURED TIME WITH COMPRESSIBLE SOLVENT FOR PUMP SHAFT TO ROTATE THROUGH THE SAME DEFINED PORTION OF THE CONSTANT VELOCITY, LINEAR FLOW REGION AS USED FOR $T_{LF}$ AT CONSTANT FLOW RATE AND SAME CONDITIONS OF PRESSURE AS $T_{MDF}$ WAS MEASURED.

FIGURE 4

APPARATUS FOR CONTROLLING A PUMP TO ACCOUNT FOR COMPRESSIBILITY OF LIQUIDS IN OBTAINING STEADY FLOW

BACKGROUND OF THE INVENTION

The invention pertains to the field of pump systems for liquid chromatography systems or other systems where it is necessary to obtain a steady flow of liquid at high pressure with an accurate composition of solvents carrying the sample to the column. More specifically, the invention pertains to the field of control systems for high pressure pumps which take into account the compressibility of fluids at high pressure in controlling solvent inlet valves to get the desired proportions of solvents used as the carrier balanced correctly regardless of variations in solvent compressibility.

Liquid chromatography systems are characterized by columns filled with small beads coated with active chemicals. Through these columns solvents are pumped which carry, in solution, samples of unknown composition which are to be assayed. These solvents may hereafter be referred to as carriers, and typically are delivered at pressures from 1,000 to 6,000 psi. It is characteristic of liquid chromatography systems that the different components in the samples move through the column at different rates of speed. Thus when a solvent carrying a sample of unknown composition of multiple chemicals is forced through the column, the different rates of movement will result in the various components emerging from the other end of the column separated in time. The identities and quantities of the various components of the original sample composition may then be determined.

Good control over the flow rate of the solvent carrying the sample through the column extends the life of the column and leads to better assay results. That is, constant flow over a long term is necessary for repeatability of the retention times of the chromatogram peaks and is a factor in the area of the peak.

The solvent must be pumped through the column at very high pressures to get a practical flow rate through the column because of the high degree of restriction to flow imposed by the column. Many solvents such as certain alcohols are appreciably compressible at these high pressures. Typically, the flow rate through the column is assumed from the number of strokes taken by the pump and the known displacement on every stroke. Thus, if the solvent compresses at high pressure the assumed volume of flow through the column calculated from the number of pump strokes taken is not the true flow volume. To further complicate the problem, it is often unknown how much any particular solvent or any mixture of solvents will compress at a given pressure, the pressure may be anywhere from 50 p.s.i. to 6,000 p.s.i., and the solvent may be composed of a mixture of only one solvent, two or more solvents in a predetermined mix or a predetermined mix of solvents at the start with a gradual change to another predetermined mix at the finish of the assay. The compressibility may be as much as 5% so errors this large can be created.

Further, to mix two different solvents using the pump which pumps the solvents through the column, it is important to know how much of each solvent is being drawn in so as to properly mix the solvents in the user defined mix proportions. A problem arises because the pressure inside the pump when the pump piston is at top dead center and ready to begin drawing in solvent is still at the column pressure which is very high. There is always liquid around the piston when it is at top dead center which forms a dead volume, and this dead volume of liquid is still compressed. Thus when the piston starts down on its intake stroke to draw in solvent, the dead volume liquid expands into the newly created volume and no new solvent is drawing into the cylinder. This creates a "front end" error of unknown proportion in that the assumption is not true that the amount of solvent drawn in on the intake stroke is equal to the displacement of the piston during the stroke. Typically, the pistons used in the pumps for liquid chromatography systems are ⅛ inch in diameter and moves only ¼ of an inch. Some companies use pistons which are ¼ inch in diameter or 3/16 inches in diameter. Thus, errors created by compressibility of the dead volume can loom large as a percentage of the total piston displacement.

Liquid chromatography columns are not well suited to handle pressure pulses in the fluid flow therethrough. Such pressure pulses result in shortening of the life of the columns. In response to this need, pumps have been developed for liquid chromatography systems which use a two piston arrangement to dampen pulses and to keep a continuous flow of fluid through the column. One such pump is described in U.S. Pat. No. 4,552,513. In such pumps two pistons are used, one of which is called the pumping piston and the other of which is called the damping piston. The two pistons are driven by a common drive train and each has its own cam which causes the stroking motion for that piston. The cam of the pumping piston is such that the stroke movement if used alone would deliver up to four times the desired flow rate during the time the piston moved up in the cylinder. The damping piston cam is shaped so that this piston moves oppositely to the movement of the pumping piston movement. When the pumping piston is moving up in the cylinder, the damping piston is moving down at three times the desired flow rate. The shape of the damping piston driving cam is such that if the damping piston were used alone to deliver solvent, the flow resulting therefrom would be equal to the desired flow rate. There is check valve at the input to the pumping piston and between the output of the pumping piston and the input of the damping piston. The result of the combined movement of the two pistons is that as the pumping piston displaces fluid at the rate four times the desired flow rate, the damping piston takes in fluid at three times the desired flow rate. The resulting output flow rate is equal to the desired rate. As the pumping piston reaches the top of its stroke and begins to move downward for the input stroke, the damping piston begins to move upward to push fluid out the output at a rate equal to the desired flow rate. The result is that a constant flow at the desired rate appears at the output of the pump if the solvents being pumped are not compressible. However, if the solvents are compressible, a lag in the flow occurs during the time the pumping piston is compressing the solvent taken in at low pressure to the pressure level of the high pressure line coupled to the column. No flow appears during this lag because until the pressure of the fluid in the pumping piston cylinder reaches the high pressure level, the check valve between the pumping piston and the damping piston does not open. Since this is the path to the output, no flow occurs at the output and an undesirable pressure pulse occurs.

Accordingly, a need has arisen for a pump control system for liquid chromatography systems and other systems operating at high pressure where a constant flow rate is needed which can maintain a constant flow rate at all pressures and for all compressibility factors.

SUMMARY OF THE INVENTION

According to the teachings of the invention, there is provided a control system for liquid chromatography system solvent pump which can sense the amount of compressibility of the solvent mix currently being pumped through the liquid chromatography system. The control system can take this compressibility into account in controlling the generation of a particular solvent mix desired by the user. In the prior art two piston pumps for liquid chromatography systems, there is an overlap period where both pistons are pumping at the same time. This overlap would cause a pulse of double flow rate and a corresponding rise in pressure. To prevent this, a pressure transducer and control system is used in prior art control systems to control the motor speed during this overlap interval so that a constant pressure is maintained. That is, the pressure transducer senses the pressure at the output of the pump and sends a signal that is used by a motor control system to regulate the speed of the motor to slow motor speed during the overlap so that a constant pressure is maintained.

The control system according to the teachings of the invention keeps a record of the amount the motor speed has to be altered to maintain constant pressure during the overlap period. By so doing the compressibility of the solvent can be continuously known for the current operation conditions, solvent mix and solvent type. This allows a constant flow rate regardless of how conditions change or how the solvent type and mix gradient is altered. That is, the control system determines the compressibility of the solvent and adjusts the motor speed to maintain a constant flow rate.

Also, the constant evaluation of the compressibility of the solvent allows the intake of new solvent on the intake stroke to be accurately calculated. That is, when the intake stroke starts from top dead center of the pumping stroke for the pumping piston, the dead volume of solvent still residing in the top of the piston must be decompressed before any new solvent enters. This is an important feature in enabling the control system to accurately calculate the times of opening of the various solvent flow control valves during an intake stroke so as to get the precise amount of each solvent needed for a particular solvent mix. That is, typically, the major solvent component supply valve is opened during most of the intake stroke and it is assumed that major solvent begins entering the pumping piston as soon as the intake stroke is started. The minor solvent flow control valves are then opened, and the major solvent supply valve closes during a linear portion of the intake stroke for times calculated to allow the proper solvent mix to be drawn into the pumping piston. Obviously, if the dead volume is expanding during a portion of the intake stroke where the major solvent is supposed to be entering the pumping piston and if this expansion prevents the major solvent from being drawn into the pumping piston cylinder, and error in the solvent mix will occur. Unless some correction for the compressibility of the solvent is made, the error will result in an incorrect solvent mix.

The amount of this decompression error depends upon the solvent mix, the pressure and compliant parts within the pumping system. The compressibility of solvents changes non linearly with the mix proportion and is not subject to any sort of accurate determination from consulting a lookup table. Thus the constant evaluation of the instantaneous compressibility of the current solvent mix at the current temperature provides a greatly improved solvent pumping system for a liquid chromatography system. This allows greater flexibility for the customer in that he or she can use any solvent desired and the system can adjust for the solvent compressibility conditions automatically. This obviates the need for providing other less accurate means which require some knowledge or effort on the part of the customer to account for the effects of compressibility. The result of the constant, real time evaluation of the compressibility of the solvents is that more control and accuracy is provided by the system to the user to get superior control over the proportions of the actual solvent mix vis a vis the desired solvent mix proportions.

BRIEF DESCRIPTION OF THE DRAWINGS

FIG. 4 is the mathematical formula used to determine the correction factor needed by the control system to account for the compressibility of the solvent.

DETAILED DESCRIPTION OF THE PREFERRED EMBODIMENT

Figure 1:
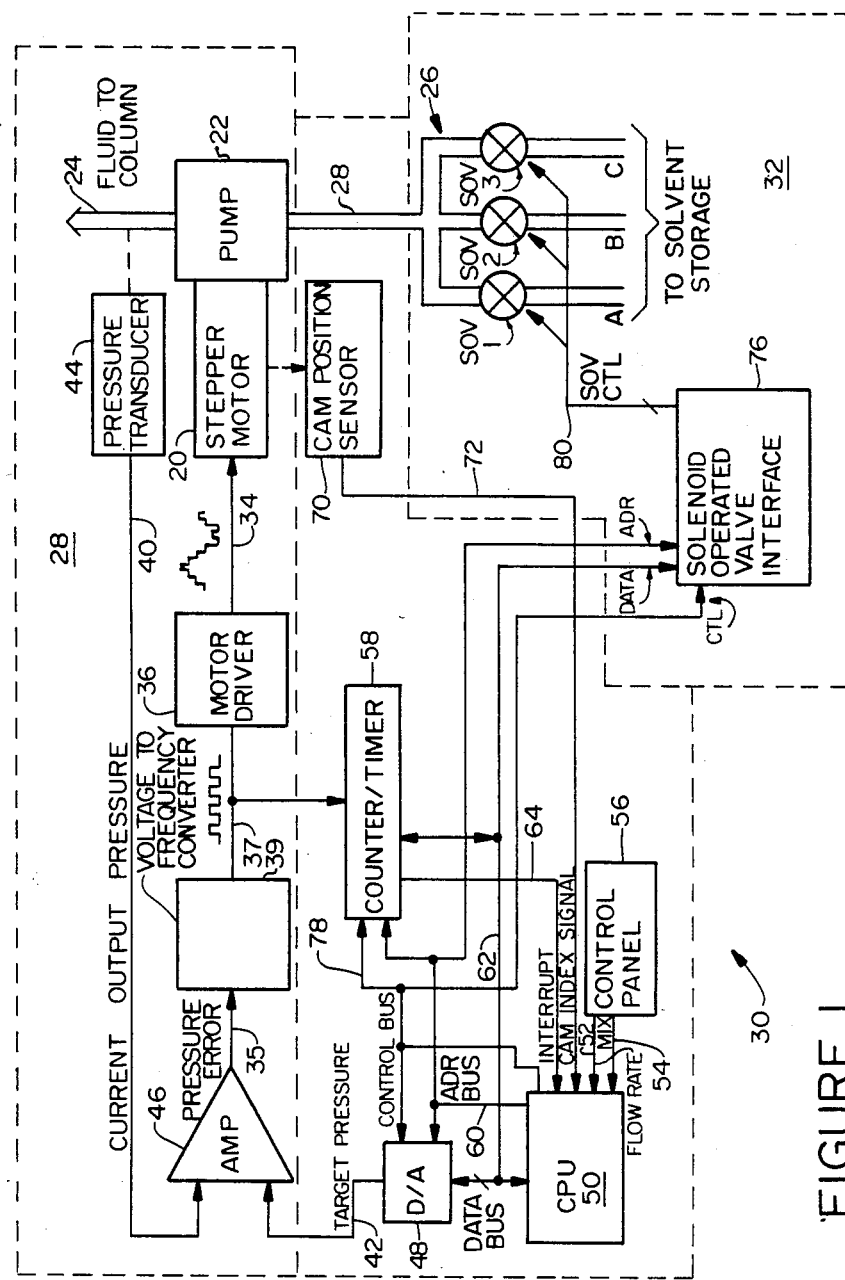
FIG. 1 is a block diagram of the control system according to the teachings of the invention.

Referring to FIG. 1 there is shown a block diagram of the apparatus according to the teachings of the invention. The purpose of the apparatus of FIG. 1 is two fold. The first function is to control the motor speed of a stepper motor 20 driving a pump 22 so as to obtain a constant flow rate of solvent carrying sample in the output pipeline 24 to the liquid chromatography column regardless of varying pressures and varying compressibility of the solvents being pumped. The second function is to control a collection of solenoid operated or electrically controllable valves, shown generally at 26, which couple various solvent reservoirs to the input port 28 of the pump 22 so as to obtain the desired percentages of solvents A, B and C in the solvent mix carrying the sample to the column (not shown).

The first function is achieved with the aid of a motor control loop indicated at 28 and a compressibility correction factor calculating apparatus shown generally at 30. The second function is achieved with the aid of the compressibility correction factor calculating apparatus 30 and the solenoid operated valves and their associated interface circuitry 32.

Figure 2:
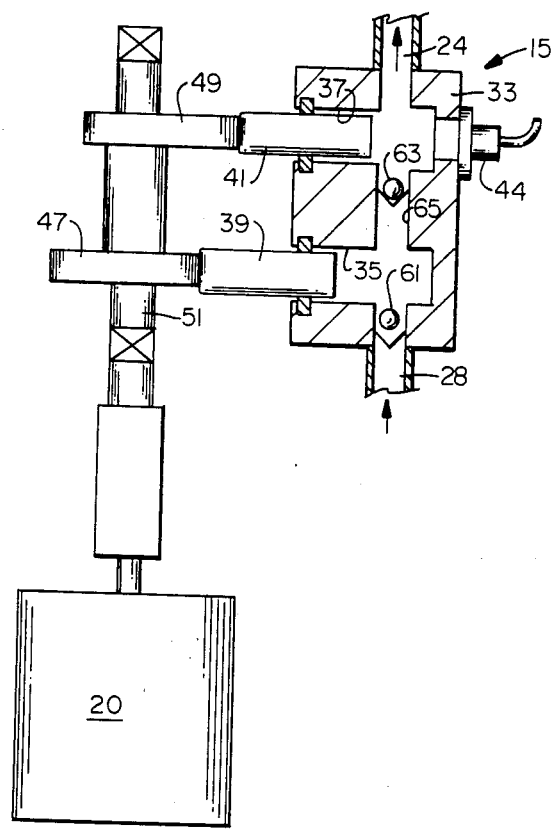
FIG. 2 is a diagram of a type of pump that may be used in conjunction with the control system of FIG. 1.

The motor control circuitry 28 operates as follows. The stepper motor 20 drives a pair of cams which in turn drive the dual pistons of the pump 22. The structure of the pump is shown in FIG. 2, and is described in detail in U.S. Pat. Nos. 4,352,513 and 4,552,513. Alternative embodiments can use pumps with two or more pumping pistons. These pumps typically have overlapping regions which could be monitored for determination of solvent compressibility. Also, some embodiments may use single piston pumps. The stepper motor receives as a driving input a signal from the motor driver 36 in FIG. 1. The motor driver will cause the stepper motor 20 to rotate a predetermined angular portion of a 360 degree revolution for every pulse it receives from the motor driver 36 on line 34. The motor driver converts the input signals it receives on a line 37 from the voltage to frequency converter 39 into a sine wave comprised of staircase like steps with 6,400 steps to a single revolution. The voltage to frequency converter converts the PRESSURE ERROR signal on line 35 to a pulse train of a frequency which depends upon the magnitude of the PRESSURE ERROR signal. The speed of rotation of the motor then depends upon the spacing of the drive pulses on the line 37.

The PRESSURE ERROR signal is derived by comparing a CURRENT OUTPUT PRESSURE signal on a line 40 to a TARGET PRESSURE signal on a line 42. The CURRENT OUTPUT PRESSURE signal is generated by a pressure transducer 44 which is coupled to the output pipe 24 to sense the pressure therein. The CURRENT OUTPUT PRESSURE signal is coupled to one input of a differential amplifier 46 the other input of which is coupled to the TARGET PRESSURE signal on line 42. The voltage to frequency converter 39 converts the PRESSURE ERROR signal into a stream of pulses on line 37 which cause the motor driver 36 to drive the stepper motor 20 to a speed which tends to change the pressure in the output pipe 24 so as to tend to reduce the PRESSURE ERROR signal to zero. In alternative embodiments, a D.C. servo motor could be used with a shaft encoder for feedback as to the motor shaft position. This arrangement could be substituted for the stepper motor and appropriate adjustments made in the driver circuitry for the motor to implement the concepts discussed above.

In alternative embodiments using single piston pumps, the compressibility could be determined by measuring the time from the first forward movement of the piston on its pumping stroke to the time the rate of change of pressure at the pump output changes sign. That is, from the time the pumping piston starts forward the pressure at the output of the pump will continue to fall if the solvent mix is compressible because the solvent will be in a stage where it is being compressed and the internal pressure in the piston is still lower than the pressure on the column. Thus the check valve will not have opened yet and the pressure will continue to bleed off the column as solvent flows through it under pressure. As soon as the solvent has been completely compressed, the check valve will open and the pressure at the output of the pump will stop falling and begin to rise. The time between this change of sign and the time the piston started forward is a measure of the compressibility of the solvent.

The stepper motor drive pulses on the line 34 are counted by a counter/timer 58. The purpose of this counter/timer 58 is to keep an ongoing record of the step number at which the stepper motor currently resides. Each step number corresponds to a particular angular position of the cam and pump drive shaft. Keeping a record of the current step number allows the computer 50 to know the stepper motor position at all times by addressing the timer/counter 58 via the address bus 60 and reading the current count via the data bus 62. A control bus 78 carries read/write control and other control signals necessary for the proper transfer of data. The counter/timer is also structured to generate an interrupt on a line 64 coupled to an interrupt port of the computer 50. This interrupt is generated during every cycle of the pump at a certain step number. This step number marks the beginning of the linear region of velocity on the velocity curve of the intake and pumping piston.

In the preferred embodiment, the solvent mixture is defined by percentages of minor solvents (less than 50% of the total volume of the mixture) in a major solvent. The mixture is controlled by the opening of the solenoid operated valves 26 during certain portions of the intake stroke of the pump. Each minor solvent has its corresponding valve opened during a portion of the intake stroke which is long enough to draw in the desired percentage of that minor solvent. Only one valve for one minor solvent is open at any particular time. The portion of the intake stroke during which each valve is open is calculated by the computer 50 and is expressed in terms of the number of steps of the stepper motor 20 during a linear portion of the intake stroke during which the valve is open. This establishes the correct mixture since the number of steps of the stepper motor 20 during the linear portion of the intake stroke piston velocity curve maps directly to a specific volume. This is because the calculated number of steps is proportional to a distance moved by the piston during the linear portion of the piston velocity curve on the intake stroke.

Because the solenoid operated valves for the minor solvents are opened only during the linear portion of the intake stroke, there must be some means by which the computer 50 is informed that the stepper motor 20 has driven the pump to the beginning of the linear velocity portion for the input piston's intake stroke. The counter/timer 58 serves this purpose by being programmed to generate the interrupt on the line 64 at the time the stepper motor 20 reaches the step at which the linear portion of the intake stroke starts.

Of course, the counter/timer 58 must be reset at the beginning of each new pump cycle (a complete pump cycle is one rotation of the pump drive shaft coupled to the motor 20). Further, the computer 50 must know when a certain reference or index point is reached in each cycle. To that end, a cam position sensor 70 is used to generate an index signal on a line 72 which is coupled to the computer 50. The index signal is generated whenever the cam reaches the index point in its rotation, and this fact is sensed by the cam position sensor through either optical or mechanical means such as a microswitch. The manner in which the cam position is sensed is not critical to the invention, and any conventional means will suffice. Upon detecting the activation of the CAM INDEX SIGNAL on line 72, the computer 50 may address the counter/timer 58 and write data to counter 58 to reset the count to zero or some other predetermined count depending upon where the index point is from the start of the pump cycle. In alternative embodiments, the counter/timer may be designed so as to reset itself to zero each time the count reaches the step number corresponding to the index point.

The computer 50 controls the solenoid operated valves 26 through a solenoid operated valve interface 76. The design of this interface is not critical to the invention, and integrated circuits are readily available which will suffice for this purpose. To turn a particular valve on or off, the computer 50 writes the address of this valve on the address bus 60 and sets the read/write signal on the control bus 78 to write. The computer then writes the appropriate data word on the data bus 62 to indicate the desired action of the valve being addressed. Typically, the address will be decoded and will enable a particular valve interface chip. This chip will then latch in the data word, decode it and generate a current signal of the proper magnitude and polarity to pass through the solenoid coil to cause the desired opening or closure to occur. These solenoid signals are coupled to the solenoid operated valves 26 via the bus 80. In alternative embodiment, solenoid operated valves will not be used. Any valve which can control flow of a liquid under the command of a computer will suffice for purposes of practicing the invention. The TARGET PRESSURE signal on line 42 is generated by a digital to analog converter 48. Generation of this signal is in response to a digital word representing the amplitude of the desired TARGET PRESSURE signal which is sent to the converter 48 by a central processing unit 50. The central processing unit 50, hereafter called the computer, runs a control program which will be described in more detail later. The purpose of this control program is to measure certain times and to calculate from these times the amount of compressibility of the solvent mix currently being used at current pressure conditions existing in the pump. The calculation results in a correction factor number which is used to adjust the TARGET PRESSURE signal on the line 42 to prevent the effects of compressibility of the solvent from altering the desired flow rate of solvent through the column. The original TARGET PRESSURE value may be established by the user depending upon the desired flow rate. The same correction factor is used to adjust the number of motor steps that the solenoid operated valve for each minor solvent is held open during the intake stroke of the pump 22 to get the desired solvent mix.

The computer 50 receives signals on lines 52 and 54 from a control panel 56. The control panel 56 allows the user of the system to establish the desired flow rate (and, consequently, the pressure at the column) for delivery of solvent through the column by manipulation of controls on the control panel 56. The signal on the line 52 indicates the desired flow rate since the pressure is generally directly proportional to flow rate. That is, the signal on the line 52 indicates the desired flow rate and the pressure which will subsequently result because of the relationship between the pressure and flow rate. The control panel 56 also allows the user to set the desired solvent mix by manipulating controls that indicate the desired percentage of each minor solvent in the mix. The data regarding the desired mix is sent to the computer on line 54.

From these values, the computer uses known routines and calculates a TARGET PRESSURE set point to get the desired flow rate. The computer also calculates the number of steps of the motor 20 that each solenoid operated valve 26 controlling an input from a minor solvent storage tank should be left open to achieve the desired mix. These calculations are done assuming the existence of either low pressure resulting in no compression of the solvent or high pressure but an incompressible solvent exists. The computer 50 then calculates the correction factor for the actual compressibility existing on each pump cycle. This correction factor is used to adjust the TARGET PRESSURE signal on line 42 to change the PRESSURE ERROR signal in such a way that pump speed is altered to maintain a constant flow rate despite the compressibility of the solvent. The correction factor is also used to adjust the number of motor steps during which the solenoid operated valves for each minor solvent are left open during each intake stroke to eliminate the effects of decompression of the dead volume of solvent in the pump 22 during each pump stroke so as to get an actual solvent mix which corresponds closely to the desired solvent mix.

Referring to FIG. 2, there is shown a schematic diagram of the pump 22 of FIG. 1. The pump, shown generally at 15, is comprised of a housing 33. Cylinder housing 33 comprised a pressurization piston chamber 35 and a damper piston chamber 37. A pressure piston 39 reciprocates within the pressure chamber 35, and a damper piston 41 reciprocates within the damper cylinder 37. The pump shown in FIG. 2 is generally like that shown in U.S. Pat. No. 4,352,636 which is hereby incorporated by reference.

The pump 15 includes the solvent inlet 28 and a solvent outlet 24. The pistons 39 and 41 are driven by respective cams 47 and 49, and the cams are mounted for rotation on a drive shaft 51. The drive shaft 51 is driven by the stepper motor 20.

The speed of rotation of the stepper motor 20 is controlled by the control circuit shown in FIG. 1 in the manner described above. A pressure transducer 44 is associated with the solvent outlet 24.

Check valves 61 and 63 are associated with the respective solvent inlet 28 and the passageway 65 between chambers 35 and 37.

The contours of the cams 47 and 49 are such that, with one notable exception, piston 41 is moving down when piston 39 is moving up toward the top of its cylinder. The piston sizes or velocities of movement are such that piston 39 causes flow out through the check valve 63 at four times the rate that piston 41 causes flow out the outlet 24 when piston 41 is moving upward toward the top of its cylinder. Thus, if the pump is operated at a speed to obtain a desired flow rate X out the outlet 24, piston 39 will be displacing a flow of 4X through the check valve 63, but piston 41 will be absorbing a flow of 3X as it moves downward. There is, however, a point in the cam profiles when both pistons have velocities which are positive, i.e., toward the top of their cylinders. This is called the overlap region, and can cause variations in the flow rate which are either positive or negative depending upon whether the transition of velocity from negative to positive for piston 39 occurs before or after the velocity of piston 41 begins to decelerate. Which case results depends upon the specific cam contours of the cams 47 and 49.

It is possible, with any one constant solvent composition, to grind the cam contours of the cams 47 and 49 to produce an essentially pulseless flow output at a given pressure level. However, even in that instance, compressibility varies with pressure level, and some regulation of the speed of rotation of the shaft 51 is desirable to negate this effect. When different solvents or different solvent compositions are used, the compressibility can vary widely, and provision for the control of the speed of rotation of the shaft 51 (to minimize pulses in the flow output) becomes even more critical.

Figure 3A:
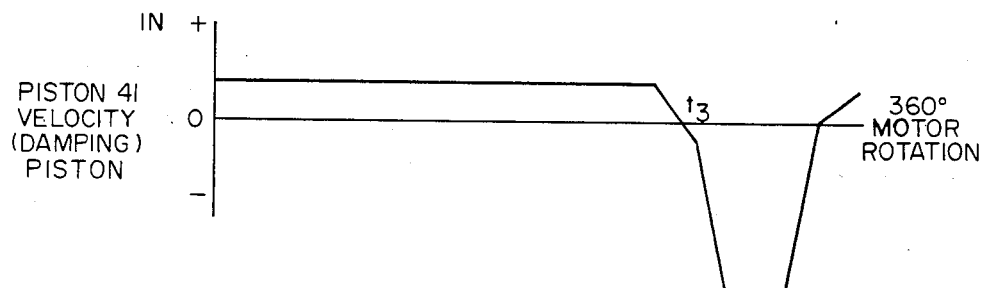
FIGS. 3A through 3C are piston velocity graphs for the pumping and damping pistons and the resulting flow rates which result at various stages in the cycles of the two pistons for different compressibilities of fluid.
Figure 3B:
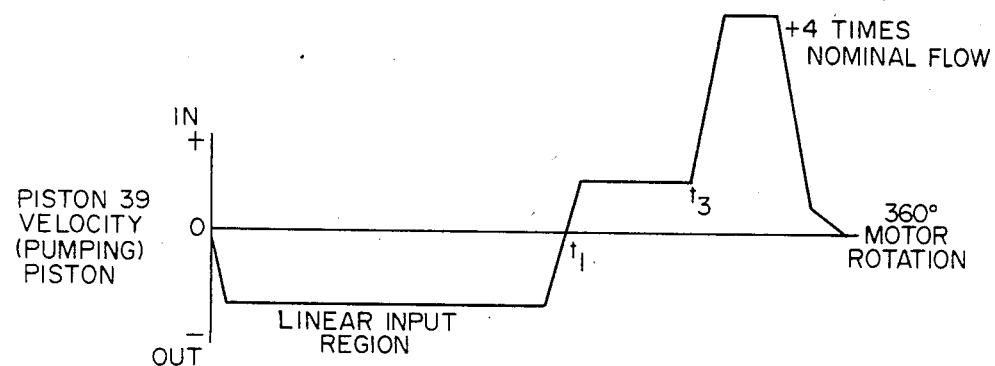
Figure 3C:
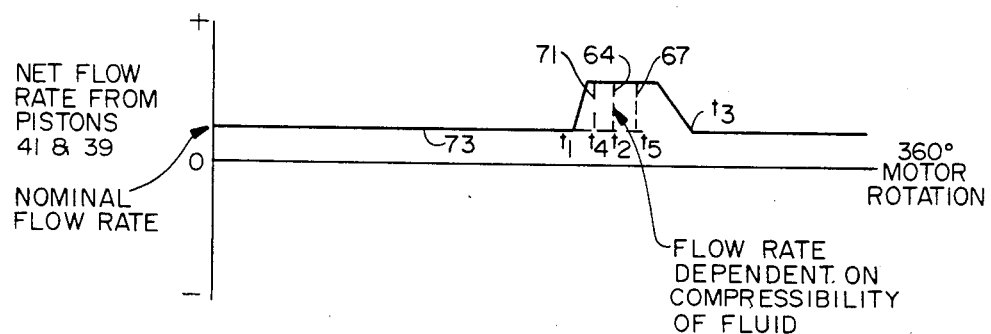

FIGS. 3A through 3C graphically illustrate the relationship between piston velocities for the two pistons 39 and 41 and the resulting net flow output from the output pipe 24 at the point of overlap in the flow caused by each of the two pistons. FIG. 3A shows the velocity of the piston 41. FIG. 3B shows the velocity of piston 39, and shows it speeding up at the beginning of its pumping stroke beginning at time t1 after completing its intake stroke (deceleration from the negative velocity of the intake stroke is shown at times before t1, and bottom dead center for piston 39 is shown at time t1).

The cam contour causing the piston velocity profiles illustrated in FIGS. 3A and 3B causes the flow profile in the overlap region between times t1 and t3 in FIG. 3C if the speed of rotation of the motor shaft 51 is maintained constant.

The effects of compressibility of the solvent at various pressures and solvent mixes is shown by the dashed lines in FIG. 3C. If the pressure or solvent mix is such that no compression occurs, then the flow rate is as shown in the solid lines in FIG. 3C. For a pressure or solvent mix which results in slightly more compression, the flow output looks as shown by dashed line 71. In this case, the piston travel that occurs between times t1 and t4 for piston 39 is not causing any flow because the solvent in the chamber 35 is being compressed as the piston 39 moves upward. At time t4, the solvent in the chamber 35 has been compressed enough that the pressure in the chamber 35 rises to the level of the pressure of the solvent in the chamber 37. At that time, the check valve 63 opens, and the flow output from piston 41 is joined by the flow output caused by the continued upward travel of piston 39. If the speed of rotation of the motor shaft is maintained constant over this period, the resulting flow out output 24 will be as shown by line 71 in FIG. 3C. If the motor shaft 51 is slowed down, the net flow rate from the two pistons may be reduced during the overlap period from time t1 to t3 to the nominal flow rate shown at 73 in FIG. 3C. The other dashed lines 69 and 67 show, respectively, the effects on flow rate during the overlap period of solvents which are increasingly more compressible. Dashed line 67 shows the effects of the most compressible solvent or the highest pressure illustrated in FIG. 3C (the dashed lines in FIG. 3C illustrate the effects of compressibility from whatever cause—the cause could be increased pressure, a more compressible solvent mix or compliant components within the pump).

Because increased flow through the column translates to rising pressure at the pressure transducer 44, the increased flow rate can be sensed and used by the control system of FIG. 1 to regulate the speed of rotation of shaft 51 to eliminate the flow and pressure pulse. This occurs as follows. When the overlap occurs, and the solvent compresses enough for the pressure in chamber 35 to slightly exceed the pressure in chamber 37, the check valve 63 opens, flow out output 24 increases, and the pressure transducer 44 senses a rise in pressure. This rising pressure changes the amplitude of the CURRENT OUTPUT PRESSURE signal on the line 40 in FIG. 1 which, in turn changes the amplitude of the PRESSURE ERROR signal on the line 38 since the TARGET PRESSURE signal on line 42 is not changed by the computer to eliminate pressure pulses. The changing amplitude of the PRESSURE ERROR signal causes the motor driver 36 to alter the pulse spacing of the stepper motor driver pulses on line 34 so as to change the speed of the stepper motor 20 in the direction to tend to reduce the flow rate. The change in motor speed tends to reduce the PRESSURE ERROR signal to zero. The response time of the control loop 28 is sufficiently fast that the pressure pulse and flow pulse are minimized.

The control loop 28 slows the motor 20 down during the overlap period to maintain a constant pressure and flow rate. The overlap period is measured in terms of degrees of rotation of the motor shaft. The amount of time it takes to rotate through the overlap region with a compressible solvent relative to the amount of time it takes to rotate through the overlap region with either an incompressible solvent or at low pressure is a measure of the compressibility of the solvent (both times being normalized to the time it takes to rotate through an arc of the same size in the linear region of constant velocity in FIG. 3A or FIG. 3B in the same conditions). The control software for the control system of FIG. 1 evaluates the compressibility of the solvent by measuring this time ratio to derive a correction factor. This correction factor is then used to correct for solvent compressibility in controlling the solenoid operated valves to obtain the correct solvent mix and to adjust the flow rate of the pump.

The mathematical formula used to derive the correction factor is given in FIG. 4. Z in the formula of FIG. 4 represents the amount of volume in the intake cylinder 35 which is traversed by the piston 39 during the overlap period, i.e., when the piston 39 is starting its pumping stroke as piston 41 is finishing its pumping stroke. To get a constant flow rate, Z must be large enough that sufficient compression of the solvent in cylinder 35 to open the check valve 63 will occur prior to the completion of the pump stroke of the piston 41, i.e., piston 41 reaches top dead center. If the solvent is not completely compressed and the check valve 63 is not yet opened at the time piston 41 reaches top dead center, then a momentary drop in the flow rate will occur while piston 41 moves downward and piston 39 continues moving upward with check valve 63 closed during the continued compression necessary to cause check valve 63 to open.

The correction factor CF is the fraction of Z consumed in the compression of the solvent in the cylinder 35 to raise it to a pressure sufficient to open the check valve 63. The correction factor is derived by measuring various times and computing the ratios between them. To understand this, consider the following. The correction factor will be proportional to the relative amount of time it takes to traverse the overlap region at constant flow rate for a compressible solvent compared to the time it takes to traverse this region at the same solvent for an incompressible flow rate. This is true because the control loop 28 in FIG. 1 slows the motor down in the overlap or double flow region sufficiently to prevent double flow from occurring. If the solvent is incompressible, the overlap region will actually result in a flow greater than the desired constant flow if the motor is not slowed down because the check valve 63 opens almost immediately after the piston 39 assumes a positive velocity. Thus the motor will have to be slowed down sooner in this case than in the case of a compressible solvent.

In the case of a compressible solvent, the check valve does not open immediately when the overlap cycle starts as illustrated by the dashed lines in FIG. 3C. The check valve 63 does not open until the solvent has been compressed sufficiently to raise its pressure to the pressure in the cylinder 37, and this time is reflected as an increase in the output flow rate symbolized by the upward portions of the dashed lines 71, 69 and 67. The dashed line 67 indicates a more compressible solvent and a resulting later slow down of the motor to maintain constant flow rate than the situation represented by the dashed line 71. Because the motor slows down later in its rotation through one cycle for compressible solvents, the time it takes to move through the overlap region for a compressible solvent to achieve a constant flow rate is shorter than the time the motor takes to move its shaft through the overlap region for an incompressible solvent.

The control system of FIG. 1 uses this fact to determine the compressibility of the solvent during each cycle. As can be seen from the equation of FIG. 4, the time to move through the overlap region for a constant flow rate and a compressible solvent, $T_{MDF}$ is calculated as the normalized ratio 80. The time to move through the overlap region at a constant flow rate for an incompressible solvent, $T_{DF}$, is calculated as the normalized ratio 82. These two ratios are then combined as another ratio and multiplied by Z to yield the fraction of Z which is not used to compress the solvent. This fraction is then subtracted from Z to give the correction factor as the fraction of Z needed to compress the solvent to the output pressure.

There are two known points for the correction factor of FIG. 4. For an incompressible solvent, CF=0 because $T_{MDF}=T_{DF}$ and $T_{LF}=T_{MLF}$. At high pressure for a compressible solvent when all of Z has been used up in compressing the input solvent to the output pressure, CF=Z. This is because the check valve 63 never opens while piston 39 is traversing Z so the motor never slows down. Thus, $T_{MDF}$ is equal to $T_{MLF}$ so ratio 80 turns out to be zero.

Typically, the times $T_{DF}$ and $T_{LF}$ are constants which are measured off line for each different operating pressure. That is, for an incompressible solvent being pumped through the column at a given flow rate, a certain constant pressure will exist and the motor will turn through the overlap angle at a certain rate and will turn through the same angle in the linear region at a certain rate. These times are constant and can be stored in a look up table for each operating pressure. Any control software which can cause the computer to store and access the necessary constants and to measure the times needed in the equation of FIG. 4 and to make the calculation shown there will suffice to implement this portion of the invention. Appendix A is the actual software used in Intel hex format and runs on a Z80 microprocessor. A flow diagram of a typical control flow for a program which can implement the control method described herein will be described in more detail below.

The control software uses the correction factor derived from making the calculation illustrated in FIG. 4 to recalculate a value AV to take into account the compressibility of the solvent. The value AV is a constant which represents the number of motor steps a minor solvent solenoid operated valve must be opened during the linear portion of the intake stroke to a obtain 0.1% by volume mix of the major solvent with that minor solvent. The constant AV is multiplied by ten times the desired percentage of that minor solvent desired in the final mix to determine the number of motor steps to keep the solenoid operated valve for that minor solvent open during the intake stroke. The control software evaluates the correction factor of FIG. 4 on every cycle of the pump and computes a moving average using the three most recent CF values. This moving average is then used to adjust AV for compressibility by the following equation:

$$new\ AV = old\ AV\ times\ [1-CF] \qquad (1)$$

The new AV is then used to control the solenoid operated valves during each intake stroke. The computer waits for the interrupt from the counter/58 indicating that the motor step at the start of the linear portion of the intake stroke has been reached. The computer then accesses the user defined desired percentage for each minor solvent. This desired percentage times 10 is then multiplied by the new AV and the step number when the solenoid operated valve for that solvent component is to be closed is calculated. The current step number is then read, and the corresponding solenoid operated valve is addressed and opened. The computer then checks the step number repeatedly by addressing and reading the counter/timer 58. When the calculated step number is reached, the solenoid operated valve is addressed and closed. The same process is repeated for all other minor solvent components for their respective percentages.

Figure 5:
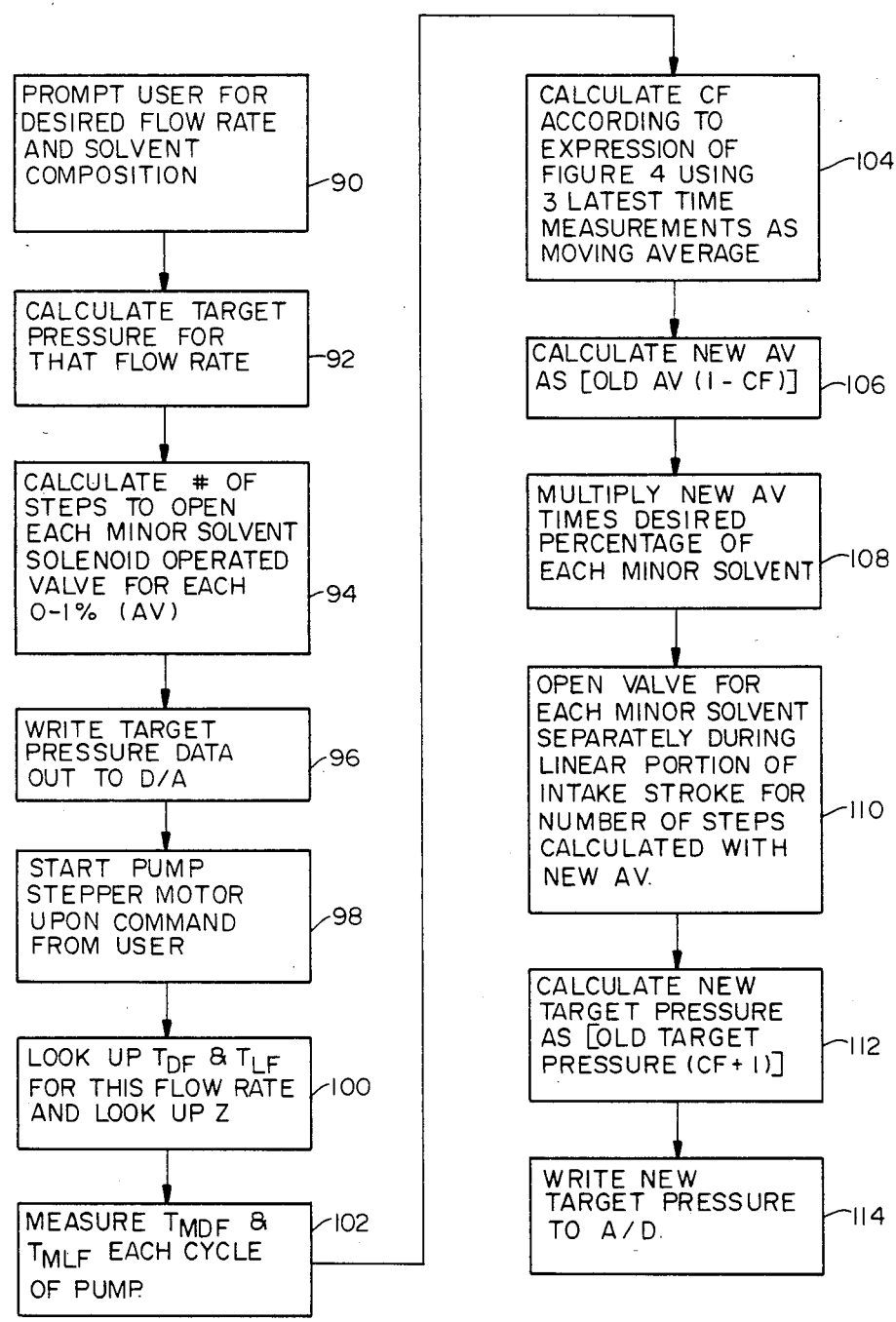
FIG. 5 is the flow diagram for the sequence of operations performed by the control system software to calculate the correction factor and control the various elements in the system based upon the result of the correction factor calculation.

Referring to FIG. 5 there is shown a flow diagram of a typical control program for the computer in the control system to cause the compressibility correction factor to be calculated and to use this correction factor to control the accuracy of the solvent mixing process and the flow rate. The actual software used to perform this process is included herewith as Appendix A in Intel hex format.

In FIG. 5, the first step is for the computer 50 to prompt the user via the control panel 56 for the desired flow rate and the desired solvent mix. The user may then enter codes which indicate the percentage of each minor solvent in the overall solvent mix and the flow rate or desired pressure. This step is symbolized by block 90. After the flow rate is entered the computer 50 calculates the target pressure needed to achieve this flow rate in a known manner in step 92.

The data regarding the desired percentages of each minor solvent is then used by the computer in a known manner to calculate the number of motor steps of the stepper motor to open the solenoid operated valve for each minor solvent in step 94. That is, step 94 determines for each minor solvent in the desired mix the number of motor steps the valve for that minor solvent should be opened during the constant velocity, linear displacement portion of the intake stroke of the piston 39. During the constant velocity portion of each intake stroke (as signaled by receipt of the interrupt from the counter timer), the computer 50 accesses this calculated data and schedules each solenoid operated valve to be opened for the calculated number of steps. Only one solenoid operated valve is open at any particular time. The number of motor steps for each 0.1% of solvent is called AV. The number of steps that each valve is opened is the desired percentage times 10 times AV. After all the minor solvents are pumped in, the major solvent valve is opened for the remainder of the intake stroke. This process is symbolized by step 94.

Next, a step 96 is performed to write the target pressure calculated in step 92 to the D/A converter 48. When the pump is started on user command in step 98, the target pressure will be the initial pressure that the control loop 28 uses to establish the error signal on line 38. After a few cycles, the target pressure will be the pressure at the fluid output 24 and will correspond to the user desired flow rate. The control loop 28 will maintain this flow rate until the target pressure is changed.

The system is now up and running but no correction has yet been made for the compressibility of the solvent. This means that the flow rate and solvent mix which the user desires has not yet been achieved because the compressibility of the solvent alters the flow rate and the amount of solvent taken in for reasons detailed above. The first step is correcting for compressibility is to look up the known times $T_{DF}$ and $T_{LF}$ stored in the look up table for the user defined pressure and flow rate at which the system is currently operating. This symbolized by step 100. The value for Z as defined in FIG. 4 is also looked up since Z may change if the cam profiles are changed, if different pump dimensions are used, or if the number of degrees in the linear flow region over which $T_{LF}$ is measured is changed.

Next, the computer 50 measures the times $T_{MDF}$ and $T_{MLF}$ as defined in FIG. 4. This can be done in any known way such as by interrupts generated by the cam position sensor 70, or by counting steps using the counter/timer 58. Any way these times may be measured will suffice for the invention as long as the angle of cam rotation over which $T_{MDF}$ is measured is the same angle of cam rotation used to measure the stored value $T_{DF}$ and the angle of cam rotation used to measure $T_{LF}$ is the same angle used to measure $T_{MLF}$. This process is symbolized by step 102.

Step 104 symbolizes the process of calculating the compressibility correction factor CF using the equation given in FIG. 4. The control software actually measures the times measured in step 102 each cycle of the pump's rotation. The three latest values are then used to compute a moving average for CF.

Step 106 represents the process of using the correction factor CF to calculate a new value for AV. The new AV is calculated by multiplying the old AV by the quantity (1−CF). Step 108 represents the step of using the new AV value to recompute the number of stepper motor steps to keep the solenoid operated valve for each minor solvent open during the linear portion of the intake stroke of the pump. Step 108 represents the process of recalling from memory the desired percentage of each minor solvent and multiplying that desired percentage times the new AV with the final result being multiplied by 10. Some embodiments may use an AV which is equal to the number of steps per each percent of minor solvent instead of the number of steps per each tenth of a percent of minor solvent. In these alternative embodiments, the final step of multiplying by 10 may be omitted.

Step 110 represents the process of opening the solenoid valves for each minor solvent during the constant velocity portion of the intake stroke of piston 39 for the number of steps calculated in step 108 for each particular minor solvent. This step is implemented by the computer 50 determining when the pump is in the linear portion of the intake stroke. This may be done by either waiting for the interrupt from the counter/timer 58 or by continuously polling the cam position sensor or the counter/timer 58 to determine when the stepper motor is on the step number marking the beginning of the linear portion of the intake stroke. The computer 50 then schedules each solenoid valve for an opening period based upon the number of steps it needs to be open as calculated in step 108 to get the desired percentage of that solvent. The computer then addresses each solenoid operated valve controller in the interface 76 and writes data causing each minor solvent valve to open in turn. When all the valves for the minor solvents have been opened, the major solvent valve is opened for the balance of the intake stroke.

Step 112 represents the process of calculating a new target pressure based upon the compressibility correction factor CF to maintain a constant flow rate over all conditions of compressibility. The new target pressure is calculated by multiplying the old target pressure by the quantity (CF+1), and writing the new target pressure data word to the D/A converter 48 for conversion to an analog signal which has an amplitude which will create an error signal of a magnitude to cause the control loop 28 to adjust to the new flow rate to compensate for the compressibility. This last operation is symbolized by the step 114.

```
:04000000F3C31348EB
:02000800ED4DBC
:04001000AF3257C3F1
:01001400C922
:04001800ED4B9CC64A
:01001C00C91A
:04002000ED439CC64A
:01002400C912
:03002800C3AF6201
:03003000C3974033
:010038007651
:04004400630629052I
:10005000880081008A0081007B007B001E4F1E4FBC
:20006600F5C5D5E5DDE5DBF9CB47CCED4EDDE1E1D1C1F1ED453E30D35FED4D3E30D37FED7C
:200086004D0018F718F50000400200740580480 9E02EC8008C01B86BFE400020013C000044
:2000A60004F401803900FF00050163AB00FF800C01C0380002000501B28F0002800C01C059
:2000C600380002000501C0380002000501B28F0002800C0137DF00010014019B6F000100D3
:2000E6000A010500050102800C01803900C08F00149C0B9C0A002C002B640064008841F90B
:200106008841F8DA68F65D7400BE7F0064006400BC02BC0280FF400000FF600000FE8000F2
:2001260000FC400000F0200000E820004000DC05004 0FC0040FC030C0CFF04000200101488
:1D0146000004500008020510001664000000806903660864006400060020000002B
:200163000907901906203004 0FF0070060040FE0074060803066419 1A271027002F020103D5
:130183001C000300056488134C4350B80B8000800200074
:20C3AD00000000000000000000000000000000000000000000000000000000000000000070
:01D8D1000056
:200196007AFE003E00F2A7017A2F577B2F5F133EFFF578FE003E00F2B901782F47792F4F66
```

```
:2001B600033EFFF53EF0F57BE601CAC401097C1F677D1F6F7A1F577B1F5FF13CC2BC01F144
:2001D600F5FE00F2E301782F47792F4F03F1E3ACE1CA02027C2F677D2F6F7A2F577B2F5FF3
:2001F600137AFE00C2020283C2020223C97CFE003E00F21E027C2F677D2F6F7A2F577B2FC2
:200216005F13D21C02233EFFF578FE003E00F23002782F47792F4F033EFFF53EEFF5782F56
:2002360047792F4F03097CFE00FA5B0229EB29D2490213EB13F13CF5C23B02782F47792F6B
:200256004F03C37102782F47792F4F030929EB29D26A0213EBF13CF5C23402F1AF7C1F67DA
:1D0276007D1F6FFF1FE00F28F02792F3C4F782FCE00477B2F5F7A2F5713F1FE00F004
:200293007B2F5F7A2F57137D2F6F7C2F6723C9C5D50E0FCDD70279D1C14FC979D60FC8FA76
:2002B300B90221FF7FC97C177C1F677D1F6F0CC3AE02C5D50600110040CDFA02CDAE027939
:2002D300D1C14FC90C7CB747CAEF02545D190D7CA8F2DE027CEE807C626B41C97DB7C2DE42
:2002F300020E00EBC3EB027AB3CA28037CB5C2080348C3280378B9CA2803FA1C037C177C9C
:200313001F677D1F6F0CC3FA027A177A1F577B1F5F04C3FA027CAAFA3803197C1F677D1F1F
:200333006F0CC3D70219C3D7027A2F577B2F5F13C3FA0278813CF5444D26006CCD9601F161
:200353004FC3D70279903CF5424B7CE603F57C177C1F577C177A1F677DE6030F0F577DE628
:12037300FC6FF1850F0F6F1E00CD0302EBF14FC3D70253
:030385003A9BC0E0
:09038800FE08C8CD70082ABCC0B3
:11039100CD1F4ECD5208CDA8120E01CD554B3A70C08D
:1003A200B7CACE04FEFFCA4E04FE0228482A02C083
:0803B2007CB5CAAA043A46C159
:0803BA00B7C4A74CAF3246C1E5
:0303C200324EC0F8
:0303C5003A72C0C9
:0603C8003D20213272C04D
:0F03CE00CD5E082805CD68081802D3FD2149C06F
:0603DD00CDF607213FC12F
:0603E300CDF60721EBC07E
:0603E900CDB2062A77C028
:0803EF007CB528042B2277C025
:0903F700DBF9E64028233A73C04B
:090400003D20203A40013273C096
:030409003A70C086
:03040C003271C08A
:05040F003EFF3270C049
:060414002A41012274C020
:0C041A00CD774CC3DC043A40013273C0C3
:030426003A70C069
:1D042900FE022005CD37091809CD9A09CD080BCD3811CD8E11CD36123E0132B2C099
:040446003D3272C011
:07044A00CD9C4CC92A74C0CF
:040451002B2274C026
:070455007CB520C13A71C023
:03045C003270C03B
:0A045F00FE0220082100002277C0F1
:0504690018AF2A77C066
:0A046E007CB5200F2A43012277C05D
:060478003A45013276C096
:09047E00C31A042A43012277C0CD
:030487003A76C002
:04048A003D3276C0C9
:09048E00C21A042100002277C00B
:060497003A45013276C077
:04049D00AF3270C04A
:0F04A100112E01CD7264C31A042100002277C00E
:0504B0003E0132E7C02F
:0304B5002AEDC06D
:0404B800233A6AC0B9
:1504BC0047E670BE782807E68FB6E67F1812F680180E3A4EC08B
:0804D100B7C82100002277C02A
:1704D900CDA74CCD774CCD5E082805DBF92F1802DBF9E650326EC0D5
:0404F000AF324EC019
:0304F400327BC098
:0304F70032B2C05E
:0304FA003286C087
:0404FD003C327AC053
:030501003272C093
:030504003126FC093
:03050700 3A53C0A4
:03050A003252C0AA
:04050D00AF32E6C063
```

```
:0305110021EFC017
:0305140022EDC015
:09051700CDB1722100002217C0D1
:030520002A23C0CB
:03052300220FC0E4
:0D052600C33612F5C5D5E5DDE5FB2191C119
:0F0533007EB728033520053610CDD4172194C389
:0805420035200C3E0132B0C16E
:03054A003A46C16D
:0A054D003DCCD33BCDCA053A46C1B0
:080557003DC28205F33A43C1E5
:08055F00B7CA74053D3243C127
:06056700C274053A6AC0EF
:07056D00F680D3F9326AC0E9
:04057400FB3A6DC021
:0D057800E6F2F601D3FAF608D3FA3AB2C063
:06058500B7283A3AE6C077
:14058B00B7202ECD5E082805DBF92F1802DBF9E680326EC040
:09059F00281B3ED7D3AF3AEFC090
:0705A800D3AF3E0132E6C0B3
:0305AF0021EFC079
:0305B20022EDC077
:0305B5002AEDC06C
:1505B80023CDB206CDCC06CDE506DDE1E1D1C1F1ED4D3AB3C026
:0805CD003CC83D20113AB4C006
:0905D5003DC0CD3C06D02ABEC099
:0405DE002322BEC056
:0405E200C93AB6C09C
:1605E600B72819CD5E082805DBF92F1802DBF9E680C8AF32B6C031
:0605FC00212C0122C0C009
:07060200CD3C06D02AB8C070
:080609007CB528062B22B8C0C5
:05061100181C2ABCC00A
:040616002322BCC01F
:0B061A002B7CB52009060AED5B4BC3EA
:06062500CDC8472ABEC04B
:04062B002322BEC008
:03062F003AB5C019
:050632003CC82ABAC01B
:040637002322BAC000
:04063B00C92AC0C048
:04063F002B22C0C0EA
:0B0643007CB5373FC0212C0122C0C055
:03064E002AC6C0F9
:0B0651007CB52B20082A500122C6C0F7
:05065C00AFC922C6C079
:0C06610037C9F5C5D5E5DDE5002AEDC080
:05066D00232322EDC073
:040672005D3AECC041
:060676009320222 1EBC0DD
:07067C00CDB206AF32E6C06B
:13068300CD5E082805CD68081802D3FD3E53D3AF21EFC0FA
:0306960022EDC092
:05069900180E2AEDC05F
:17069E003ED7D3AF7ED3AF23CDB206DDE1E1D1C1F1FBED4D3A6AC04B
:0B06B50047E670BEC83A77013243C12F
:0906C00078E68FB6E67F326AC0CD
:0706C900D3F9C9F33A43C164
:0706D000B728063D3243C1CB
:0506D700200A3A6AC090
:0706DC00F680D3F9326AC079
:0506E300FBC9218CC0E1
:0506E80035C03A8BC093
:0406ED00772149C068
:0606F100CDF6073248C0FF
:0606F7005F16002A4AC054
:0406FD0019224AC0B4
:0C070100CDFD07CDCA0EC2D007216FC08D
:09070D00CB46201CCBC63A70C09B
```

```
:07071600FE0228133A86C021
:06071D00B7200A2184C090
:0D0723007EB72806351803CD02093A6EC0D6
:06073000B7C8AF326EC035
:030736003A52C074
:06073900B7280C2A4AC09B
:03073F00224CC089
:060742002100000224AC064
:04074800AF3252C0BA
:04074C003C327CC0FF
:03075000032BAC02A
:030753003289C028
:03075600217DC042
:110759007EB728033518103A3C01773A3D01327EC0FC
:06076A003A3E01327FC09F
:030770003A4FC03D
:09077300FE05F29F07473A7AC027
:06077C00B728073A53C044
:030782003252C030
:07078500C90420163A81C0EF
:08078C00B720103E013286C0C7
:0507940018092A17C03E
:030799002215C066
:09079C00CD2B162100002217C02C
:0307A5002246C029
:0307A8002112C05B
:0F07AB007EB72808343E28BE300236003A7CC0A4
:0607BA002F3C3C327CC024
:0407C000C8327BC000
:0307C4003A52C0E6
:0407C7003C3252C0AE
:0407CB00AF326FC01A
:0407CF00C92A17C05C
:0407D300232217C006
:0307D7002148C0F6
:0607DA005E16002A46C075
:0407E000192246C0D4
:0407E400ED5B54C0B5
:0807E800AFED5230A93A4FC0F9
:1007F000FE05F22D07C9DB8F477E9070C93A70C0A5
:05080000B7C03A86C0FC
:07080500B7CA4C082A0AC023
:04080C00ED5B39C0A7
:09081000AFED52DA4C082A02C0D7
:04081900ED5B37C09C
:0D081D00AFED52DA4C082AF700ED5B4AC03F
:20082A00AFED52380B2AF900AFED5228153813C92AFB00AFED52D82AFD00AFED52280338B8
:07084A0001C93E01324EC05E
:05085100C9DD2A9BC374
:0B085600DD23DD23CDBD4EC93A3EC3BB
:05086100B7C93A3FC3D6
:0D086600B7C9DBF9E680C0D3FDC93A84C0F4
:0A087300B72017113601ED53A9C19B
:09087D00CD7264CD02093A85C078
:0A088600B7C8CD326418383A87C0B5
:04089000047 3A86C09D
:05089400B8C83287C066
:17089900B7060128 08CDC42021131D181004CDB92021181D3A70C0C6
:0908B000B7200321221D3AB3C157
:0608B900B720093AB3C0AC
:0A08BF003D2803CD9922ED5B49C3EB
:1508C900CDC847FDE5CDB458380EFD36000121E408ED5B4BC3A6
:0908DE00CDD847FDE1C93A82C002
:0D08E700B7C262592162590 60BED5B4BC38D
:0608F400C3D8473A86C09C
:0E08FA00B7060120010418C33A3F013284C042
:20090800C90011940118031196 01DDE5DD19DD5E00DD5601DDE1C9D51194011804D51196DC
:1309280001DDE5DD19DD7500DD7401DDE1D1C9ED5B06C0F9
:03093B002A0FC0C0
:08093E00AFED52304F3A7BC0CF
```

```
:08094600B7C8CD660E3A52C09D
:17094E003007FE02CA7A09180AFE04CA7A090000000000AF2A15C0EF
:04096500ED5B13C073
:09096900ED5238193E01327AC04A
:030972002A06C092
:03097500220DC090
:060978001818AF327AC02E
:03097E002A0FC07D
:03098100220DC084
:07098400180C3EFF327AC09F
:03098B002A0FC070
:04098E002B220DC04B
:07099200CD2A70AF327BC0DB
:04099900C93A79C01E
:06099D00B7C8ED4B02C0DB
:0A09A30078B12009210000220DC0E8
:0709AD00C3940AAF327BC0C6
:0309B40032B2C09C
:0309B7003286C0C5
:0609BA00CD990A3A79C054
:0C09C000FE01CA370AFE02284E3A7AC037
:0609CC00B720062A0DC051
:0309D200220FC031
:0309D5002A06C02F
:0309D800220DC02D
:0509DB003E01327AC06C
:0509E0003E06324FC08D
:0609E5002100002217C0F2
:0309EB002246C0E1
:1309EE00DD21A900CD660E3004DD21B000CDD10A2215C08D
:0D0A0100DD23DD23DD23CDEA0AAF3252C034
:030A0E002149C0BB
:0B0A1100CDF607C3940A3E04324FC02C
:1E0A1C00DD21BA00CD660E3004DD21C100CD5B0E3804DD21C800CDEA0A185D2A04C074
:070A3A007CB520063AB3C0B1
:080A41003C20D33E01324FC0FE
:130A4900DD21E800CD660E3004DD21EC00CDEA0A3A7AC020
:060A5C00B720062A0DC0C0
:030A6200220FC0A0
:030A65002A0DC097
:040A6800ED5B23C05F
:0E0A6C00AFED52EB210000CD9601ED4B04C022
:060A7A00CD03022A23C097
:040A800019220DC06A
:040A8400EB2A0FC08A
:0C0A8800AFED523E0138023EFF327AC052
:040A9400AF3279C044
:170A9800C921B50A5E235623EBAFED42EB3004232318F17E3251C0AC
:050AAF00237E3250C05F
:200AB400C9280000005000000100A0000101F000020212020203D0020306DC05040821010047
:150AD400CDD30EDD5E00DD5601DD6E022600CD0302EB2213C0CB
:080AE900C9F3DD7E003253C0A9
:030AF1003252C0BE
:090AF400DD6E01DD66022254C032
:060AFD00DD7E03328BC018
:030B0300328CC071
:050B0600FBC93A7BC0B1
:080B0B00B7C8CDA40B2A25C0D8
:050B1300E9ED4B15C0E7
:030B18002A0DC0E3
:030B1B00220FC0E6
:040B1E00ED5B23C0A8
:130B2200AFED52EB7AB7210000FA3C0BCD9601ED4B13C0E5
:060B3500CD03022A23C0DB
:040B3B0019220DC0AE
:040B3F00ED5B0FC09B
:0C0B4300AFED523E0130023EFF327AC09E
:050B4F00184E2A0DC044
:030B5400220FC0AD
```

```
:030B57002A15C09C
:040B5A00ED5B13C07C
:060B5E00AFED522219C0A8
:050B640038173A88C0BB
:070B6900FE013E013288C0CD
:0B0B7000CDAB0FCD46033E01327AC032
:050B7B00181C3A88C0BF
:060B8000B73E003288C000
:130B8600CDAB0FCD5703060111003FCDFA023EFF327AC0E5
:060B9900CDAE02220DC0EA
:040B9F00AF327BC036
:040BA300C93A4FC03C
:130BA700FEFF2068CDDA0E5E2356EBCDA202EB413A29C07F
:040BBA004F2A27C0D7
:090BBE00CD4603CDC5022213C08F
:060BC700CD0A0E3A12C037
:0D0BCD00B7200CCD750E30103E013212C065
:0E0BDA00182AFE083005CD750E38213A7AC073
:0C0BE800B7201B21510BCD660E3A52C005
:180BF4003006FE02280C180DFE04C2090C0000000000219F0B2225C0AF
:130C0C00CDCA0ECCEC0EC9B7201CCDCA0EC2AB0B3A50C047
:080C1F00B7CAAB0B3D3250C017
:080C2700C2AB0B3EFF324FC0CF
:110C2F00C3AB0BFE012041CD750E300B3E013283C09C
:050C40003E033279C003
:080C4500C9CDDA0EED5B15C00C
:090C4D00732372219F0B2225C0C4
:070C5600CDCA0EC02183C0CE
:0A0C5D007EB72806353E033279C049
:060C6700CDEC0E3A50C076
:090C6D00B7C2050E3EFF324FC074
:200C7600C9FE02202EDD21DA00CD5B0E3804DD21E100D5C1CDD10ACD0A0E21510B2225C077
:1B0C9600DD21E800CD660E3004DD21EC00CDEA0AC3050EFE03204FED4B02C0FD
:160CB100DD21CC00CD660E3004DD21D300CDD10ACD0A0E3A7AC01C
:060CC700B7280D3A53C0EE
:030CCD003252C0E0
:060CD000219F0B2225C04C
:070CD600C921510B2225C0CA
:070CDD00CDCA0EC03A51C060
:040CE4003D3251C08C
:200CE800C0DD21DD00CD5B0E3804DD21E400CDEA0AC3050EFE04C28D0DDD21B700CD660E12
:170D08003004DD21BE00CD5B0E3804DD21C500D5C1CDD10A3A7AC0FD
:060D1F00B7280D3A53C095
:030D25003252C087
:060D2800219F0B2225C0F3
:090D2E00C9CDCA0E28132A15C014
:030D3700221BC0BC
:030D3A002A0DC0BF
:030D3D00221DC0B4
:060D400021140B2225C066
:040D4600C92A15C0E1
:030D4A00221FC0A5
:030D4D002A0DC0AC
:030D50002221C09D
:0C0D5300CD3A0FCD0A0E21510B2225C015
:030D5F003A51C046
:080D6200B720163E02324FC01B
:200D6A00DD21DD00CD5B0E3804DD21E400CDEA0AC9DD21CF00CD660E3004DD21D600CDEAE3
:0A0D8A000A1878FE05201D2A15C086
:040D9400ED5B13C040
:080D9800AFED52383E2A06C0FF
:030DA000220DC061
:050DA3003E01327AC0A0
:050DA8003E06324FC0C1
:070DAD00C9219F0B2225C0A4
:040DB400ED5B06C02D
:030DB8002A0FC03F
:0A0DBB00AFED5220073E05324FC095
:070DC50018143E01327AC050
```

```
:040DCC00EB220DC049
:030DD0002A15C021
:040DD300ED5B13C001
:080DD700AFED52D0AF327AC03B
:030DDF002A0FC018
:030DE200220DC01F
:030DE5003A4FC0C2
:200DE800FE062819DD21BA00CD660E3004DD21C100CD5B0E3804DD21C800CDEA0A214FC091
:050E080035C92A13C0EA
:200E0D007CB52830CDA202EB410E01210040CD5703C5E5CD660E3009ED5B09013A0B011834
:200E2D0007ED5B03013A050147CD3C037CB7E1C179FA540ECD660E30082A09013A0B01180A
:0A0E4D00062A03013A0501222DC018
:030E5700322FC077
:080E5A00C9210700ED5B02C095
:0A0E6200AFED52C9C5E5ED4B3BC0F2
:030E6C002A02C097
:0C0E6F00CD1914E1C1C9CD660E3A52C085
:120E7B003005FE022009C9FE04C800000000002A13C077
:030E8D003A4FC019
:070E90003C2814ED4B02C0E9
:140E9700DD21F000CD660E3004DD21F300CDD10AED5B15C02E
:160EAB00AFED527CB7FC0D4AEB016400210000CD9601ED4B13C0DD
:0C0EC100CD0302EB3AF600BDC93A53C065
:040ECD00473A52C08E
:0C0ED100B8C9CD1914D0444DC92154C03B
:030EDD003A52C0C6
:060EE000B720033A53C0E5
:090EE60047232310FCC93A2CC07B
:040EEF004F2A2AC09C
:200EF3003A6E0147ED5B6C01CD57033A6B0147ED5B6901E5D5C5CD3C037CB7C1D1E1F03A19
:200F1300710147ED5B6F01E5D5C5CD3C037CB7C1D1E1F22A0FEB410E01210040CDFA027913
:030F33002227C0B2
:030F36003229C09D
:040F3900C92A02C0FF
:0B0F3D00ED5B9F00AFED52D02A1BC0FF
:040F4800ED5B1FC07E
:170F4C00AFED52E57CB7FC0D4AED5BA100AFED52E1D8E5ED4B1FC0A9
:040F6300ED5B21C061
:0C0F6700210000CD9601E5D5ED4B1BC02C
:040F7300ED5B1DC055
:1F0F7700210000CD9601EBC1AFED42E3EBED52D1C1CD03027AB7F2930F1100002A23C0F8
:140F9600AFED527CB7FC0D4AED4BA300AFED42D0ED5323C027
:040FAA00C93A2FC051
:060FAE00280A473A4FC07B
:0B0FB4003C782002D63047ED5B2DC0DA
:130FBF00CDD50FCD0B100601110040CDFA02EB412A0DC042
:080FD200C3A202C5D52A0DC01F
:0F0FDA007CB52003210100CDA20241EB2A23C0E8
:1E0FE900CDA202CD5703EB410E01210040CD3C0379D1C14FCD460341EB78ED5330C066
:031007003232C0C2
:04100A00C92A19C016
:11100E007CB7F5FC0D4AE5CDA202CD460379223DC052
:03101F00323FC09D
:04102200D13A4FC0B0
:201026003C2802F1C9F1C5E5FA7A10CDE910ED5B36013A380147CD3C037CB7E1C1FACA10B7
:031046003A81C02C
:09104900B7201ECD660E3A7EC0F0
:08105200300 2D6033D327EC0DE
:05105A00200E3286C0EB
:04105F003C3281C0DE
:031063003A80C010
:041066003C3280C0D8
:03106A003A8AC0FF
:0B106D00B7284F210000AF4F328AC0AF
:1D1078001845CDE910ED5B39013A3B0147CD3C037CB7E1C1FACA10CD660E3A7EC08B
:081095003002D6033D327EC09B
:05109D00200E3286C0A8
```

```
:0410A2003C3281C09B
:0310A6003A80C0CD
:0410A9003C3280C095
:0310AD003A89C0BD
:0B10B000B7280C210000AF4F3289C0B0
:0410BB003C328DC076
:0E10BF00C5E5CD0C11CD2A70E1C1C93A81C042
:0910CD00B728EFCD660E3A7FC092
:0810D6003002D6033D327FC059
:0510DE0020DF3281C09B
:0410E3003C3286C055
:0B10E70018D6EBCDA202C5E52A13C00D
:1610F2007CB52003210100CDA20279EBE1C147CD5703792240C0F2
:031108003242C0B0
:08110B00C9CDCA0EC03A8DC027
:0A1113004FB7280137060C218FC0EA
:0F111D007E17772310FA17E601B9280A218EC032
:0B112C00B7200334180135AF328DC02E
:04113700C93A4FC0A2
:06113B003C201321AFC0AF
:09114100CDF6072A460122ADC0DB
:06114A0021000022B0C0EC
:04115000C921AFC042
:09115400CDF6075F16002AB0C0B9
:04115D001922B0C0E3
:031161002AADC0F4
:041164002B22ADC0CD
:091168007CB5C02A460122ADC08D
:031171002AB0C0E1
:081174007CB521000022B0C08F
:04117C00C02A0FC0B6
:08118000ED5B480119220DC0CE
:051188003E01327AC0B7
:04118D00C93A7AC021
:06119100B728332A0FC04D
:04119700ED5B0DC03F
:08119B00AFED5228273A7AC09B
:0F11A300B7FAB7117CB7F2C711CDD0112A0FC020
:0411B20023220FC025
:0C11B600C97CB7FAC711CDD0112A0FC0B8
:0411C2002B220FC00D
:0511C600C9AF327AC040
:0311CB002A0DC02A
:0511CE00FBC92A0DC061
:0411D300ED5B0FC001
:1D11D700AFED527CB7FC0D4AED5B1A01193806ED4B1C011842ED4B3201ED5B0FC09C
:2011F4002A1E01193806ED4B2001182E2A2201193806ED4B240118222A2601193806ED4B81
:20121400280118162A2A01193806ED4B2C01180A2A2E01193804ED4B3001C50B78B120FB05
:05123400C1C93A70C0C1
:07123900B7CA58123A86C043
:07124000B72815E52A02C0E2
:0A1247007CB5E1280CE5ED5B08C062
:0B125100AFED52E1DA9212ED4B06C047
:19125C00CD19143837000000AF08CDE1127CD3DC7DD3ECD3FCED5B23C038
:031275003A70C00C
:0E127800FE02200A3E0108CDE112ED5B23C00C
:0B128600AFED523003210000220AC02F
:0F129100C9ED5BFB431804ED5B3543ED53A9C179
:0712A000CD7264AF3270C093
:0512A700C9E53A70C02A
:0912AC00FE022820AFED5B33C007
:0B12B500ED523813E1E5AFED5B35C0F2
:1712C000ED5238040602180A060818060608180206 0AE1F33A6AC0D6
:0612D700E6F5B0326AC02A
:0F12DD00D3F9FBC93A0E0147ED5B0C013A70C023
:2012EC00FE02280DDBF9E60AC03A110147ED5B0F01CDA20208B72805CD46031803CD570389
:04130C00CDAE02C997
:031310003A9BC045
```

```
:06131300FE09C83A4FC0BC
:0A131900FE0338033C20073A88C1A8
:07132300B7C46A163AE6C0E8
:06132A00B7280432E7C001
:04133000C921E7C028
:091334007EB7C83600AF32E8C0F4
:08133D00CD2D14200721EAC0A8
:09134500AFBE28143E0132E8C0DD
:03134E0021EAC0D1
:0C1351007EB728033518113E0232EAC0B6
:03135D002ABAC0E9
:0C136000CD1F4ECDCD14CD73151101C171
:03136C002AD8C0BC
:05136F00444D2ADACC24
:08137400CD191438152ADCC064
:10137C00CD19143824CDDA13CDC6130E102ADEC0C5
:07138C0018724D442ADCC079
:10139300CD1914380DCDDA13CDB2130E202ADEC0C9
:0D13A300185BCDB213CDC6130E402ADEC07C
:0613B000184ED52AE0C032
:0413B600ED5BD8C053
:0913BA000E10CD9B14ED53E0C0B0
:0713C300D11828D52AE2C071
:0413CA00ED5BDAC03D
:0913CE000E20CD9B14ED53E2C08A
:0713D700D11814D52AE4C06F
:0413DE00ED5BDCC027
:0913E2000E40CD9B14ED53E4C054
:1D13EB00D10E40EB147BB7280473237123I5EBC8EB360018F5E5D52A570111EFC04D
:09140800CDEE13D1E17932EBC005
:07141100CDEE137B32ECC0AD
:1E141800C97995789CC9AFCB1CCB1DC9EB210000CD9601EBC906002A5B01ED5B02C001
:0C143600AFED52D29514CA95142ABAC02A
:09144200CD1F4ECDCD142ACFC000
:03144B003AD1C0D3
:18144E004FCDC50206007CB5280BED5B5901AFED523002CBE02AD2C010
:031466003AD4C0B5
:161469004FCDC5027CB5280BED5B5901AFED523002CBE82AD5C0F2
:03147F003AD7C099
:171482004FCDC5027CB5280BED5B5901AFED523002CBF07832E9C03C
:05149900B7C93AE8C0EC
:0C149E00B7280FE5D5C5CD2D143AE9C0E4

:1214AA00C1D1E1A12003EB1803110000E5D5EB2ADEC075
:0614BC00AFED5222DEC07C
:0814C200300621000022DEC00B
:0714CA00D1E1C9E52AC4C00D
:1214D100CD1E147CB52003210100CDA202EB412AC2C04B
:0D14E300CD1E14CDA202CD57037922CCC03E
:0314F00032CEC039
:0314F3002AC8C044
:0714F600CD6115DD2A9BC347
:1014FD00DD6E04DD6605CDA202CDFA027922CFC0E4
:03150D0032D1C018
:031510002ACAC024
:13151300CD6115DD6E06DD6607CDA202CDFA027922D2C080
:0315260032D4C0FC
:07152900CDC502E52ACFC089
:031530003AD1C0ED
:1C1533004FCDC502D1E519EB21E803AFED52D17CB7F2551519CDA2027922CFC0F1
:03154F0032D1C0D6
:0A155200210000CDA2027922D5C0CD
:03155C0032D7C0C3
:0A155F00E1C9CDA202EB412ACCC085
:031569003ACEC0B7
:16156C004FCD4603EB41C91830ED5B54013A560147C5D52A0DC0C1
:20158200CDA2023A620147ED5B6001CD4603EB410E01210040CD3C0379D1C14FCD4603EB32
:0615A20041C5D53A87C1E6
:0515A80047ED5B85C169
:0515AD00C5D52ACFC0E6
```

```
:0315B2003AD1C06B
:0C15B5004FCD4603E5C5CDC50222D8C0CD
:0815C100C1E1CD1C1622E0C0BF
:0715C900D1C1C5D52AD2C033
:0315D0003AD4C04A
:0C15D3004FCD4603E5C5CDC50222DAC0AD
:0815DF00C1E1CD1C1622E2C09F
:0515E700D1C12AD5C0AE
:0315EC003AD7C02B
:1415EF004FCD4603E5C5CDC5027CB7F2001621000022DCC02B
:08160300C1E1CD1C1622E4C078
:03160B002AD8C01A
:04160E00ED5BDAC0F6
:0516120019ED5BDCC0D6
:041617001922DEC0F6
:10161B00C93A5F0147ED5B5D01CD4603CDC502C9FC
:03162B003A52C070
:06162E00B720033255C194
:07163400CD5C16ED5B15C053
:06163B007323723A55C151
:041641003C3255C121
:1216450047CD660E3A750130033A7601B8C0AF3255C108
:041657003C3288C1D8
:04165B00C92156C18A
:03165F003A55C138
:0B166200B7C847232310FCC93A54C14D
:0A166D00B7C0CD660E301E2A5AC128
:07167700CDA20279328EC101
:03167E00228CC1FA
:05168100E5C52A58C177
:07168600CDA20279328BC1F5
:03168D002289C1EE
:0816900018321E02DD2164C1C5
:0F169800CD76170602110040CD570379328EC16F
:0316A700228CC1D1
:0816AA00E5C51E04DD215EC14F
:0F16B200CD76170603110040CD570379328BC157
:0316C1002289C1BA
:2016C4003A650147ED5B6301CD460359C1414BD1D5C5CD3C0359C14BD1CD57037CB4FA4C6D
:0516E4001779322CC053
:0316E900222AC0F2
:2016EC00CD5117CD57033A6B0147ED5B6901E5D5C5CD3C037CB7C1D1E1F24C173A7101476A
:20170C00ED5B6F01E5D5C5CD3C037CB7C1D1E1F2201741EB0E01210040CD3C033A5601472B
:0C172C00ED5B5401CD4603E5C51184C1FE
:031738002181C14B
:0B173B00010600EDB8C1E179327EC16B
:03174600227CC141
:07174900CDA717AF3288C1E4
:06175000C9E5C53A8BC19A
:041756004F2A89C1CC
:03175A003A8EC103
:05175D0047ED5B8CC1AB
:20176200CD57033A680147ED5B6601CD460359C143EBE1C9DD6E00DD6601DD2BDD2B1DD50E
:20178200CDA20241EBD5FDE1DD6E00DD6601DD2BDD2BD11DD5CDA202FDE5D1CDFA02D17B5C
:0817A200B7C8D518DE3A7EC17C
:0417AA004F2A7CC185
:0317AE003A81C1BC
:0517B10047ED5B7FC164
:0617B600CDFA023A84C1E5
:0517BC0047ED5B82C156
:0F17C100CDFA020602110060CD5703793287C1BD
:0317D0002285C1AE
:0117D300C94C
:0317D4003A90C187
:0E17D700CB472810CB4FC8CD1C18C803A90C18C
:0517E500CB8F3290C122
:0817EA00C9CD1C18C82190C1F3
:2017F200CBC6CBCE2E003E1EB3ED793717E61F67ED78E63FFE3F20097D826F7C10EA2C1838
:09181200042C1F38FC7D328FC14B
```

```
:0A181B00C9060516060EF83A6BC068
:20182500E6E05FED79ED78E63FFE3FC9010000000000020000000000030000000000004007E
:20184500E518B4220503E518A4220602E5183D260700E5180B230800E5185C230900E518C1
:201865009C240A02E51819260B02E5181D260C02E51821260D02E51825260E02E518292609
:201885000F02E5182D261002E51831261102E51835261202E518392613011519DD26140147
:2018A500451951321501751989331A04E518EC341601A51902351800D519833519000051AA5
:2018C5009C351E01351A04361D01651A7B361B01951AED361C01C51A633E1700F51AE03E6D
:2018E5004E4F2048454C5020202020202020202020202020202020202020202020202020DD
:1D190500202020202020202020202020202020454449542048454C50202020D6
:201922002020202020202020202020202020202020202020202020202020202020202020A5
:2019420020202044454C54452048454C502020202020202020202020202020202020E9
:20196200202020202020202020202020202020202020534F5242204845C502020CF
:20198200202020202020202020202020202020202020202020202020202020202020202045
:2019A200202020484F4C442048454C50202020202020202020202020202020202020D5

:2019C200202020202020202020202020202020202020202053544F502048454C502020202096
:2019E20020202020202020202020202020202020202020202020202020202020202020E5
:1D1A020020202053544154455320484544C502020202020202020202020205A
:201A1F00202020202020202020202020202020202020202020494E49544941C495A45F5
:201A3F002048454C5020202020202020202020202020202020202020202020202020DE
:201A5F002020202020205055525447452048454C5020202020202020202020202020DB
:201A7F002020202020202020202020202020202020202054455354204845C5020DE
:201A9F00202020202020202020202020202020202020202020202020202020202027
:201ABF002020202020434F4E54494E5545204845C50202020202020202020202020F9
:201ADF00202020202020202020202020202020202020534441524254204845C5050
:1D1AFF00202020202020202020202020202020202020202020202020202020202A
:201B1C00202020202020202020445535420C6494C4520CC4F4720D25332333220CD4F442B
:201B3C0045D3595354454D20D455524E4F4646202020202020202020444941474E4F46F53D6
:201B5C005449432020202020204E5544245253797374656D2053657269657320F542D
:201B7C00657374202320327878526F6D20546573742020202020202020202020323088
:201B9C003052616D2054657374202020202020202020202023303127537320436865C
:201BBC00636B73756D204D6F6E69746F722023203032466C6F7720536B6162696C697479D
:201BDC002020202020203230336368656376616C75652049646E74656777269747920323037
:1D1BFC00344D6F746F722053746570204D6F6E69746F7220203230354D6F746F2D
:201C19007220456E61626C65204D6F6E69746F72203230364D6F746F20537465702054D1
:201C390065737420202020202023203037536F6C656E6F6964206656616C7565205465737420AB
:201C5900203230385365742046756C6C205363616C652044616320202032303953657420B
:201C79004175746F7A65726F2020202020202020203231304D6F746F7220537465702F56ED
:201C9900616C7565205465737423313020202020202020202020202020202020202020AF
:201CB900203231325072672073616D26667572736696F6E202020203231334669696E65C65A2
:201CD900202020204D6178202020202020204D696E202020544968652025412020202527
:1D1CF90042202020254320464C6F775053494241524D5061494E49542020524423
:201D160059204E52444E9204E52554E2053544F502050555252420484F4C4454696D6520E8
:201D3600202541202020254220202254320202050535349204669626C65205374617420466C46FE
:161D5600076F4F204D617850204D696E502021221DCD99222183C2F9
:081D6C000630CD8840214FC272
:081D74000630CD884021 19C2A0
:081D7C000630CD884021B5C2FC
:081D84000630CD884021B5C1F5
:0B1D8C000660CD884021E91D11B5C2A2
:041D9700ED539DC1AA
:091D9B000011000EDB0EB3A9DC30C
:161DA400C630772311F91DEBCD63082015010C00EDB0EB3A44C344
:141DBA005F1600CD5840CD7A40EB1805010700EDB03A01C00C
:201DCE00B7280821051E011000EDB021B421CDBB21CDD321CD3820CDA320C95350383830FB
:201DEE00302020202046494C4520204C4F41444445EEE942050524550204845414433
:0A1E0E0020494E205553453A95C176
:081E18005FFE16280B3A95C18C
:061E2000FE19C03AB1C139
:051E2600B7C03AB0C195
:061E2B00B7C8AF32B0C1E0
:151E31007BFE162007CD5D35CD4120C9CD561ECDC51E2A9DC117
:031E460011E5C1E2
:121E4900AFED522004CD4120C9CD3820C93E013292C1CC
:031E5B0021E6C2BB
:201E5E00CDEE46CDCD14CDC846CD051FCD7640CD2E47CD7640CD3747CD7640CD4047CD763C
:0A1E7E0040CD5C47CD76403A9EC38C
:091E8800C63077230E203AA4C3F2
:0E1E9100B728020E2A7123CD7A40EB2103C33D
:201E9F00010500EDB0EBCD0947CDA121CD7640CD4A47CDA121CD7640CD5347CDA121CD76BD
```

```
:051EBF0040AF3292C1AA
:041EC400C911B5C1CA
:061EC80021311D3AB3C1F7
:1E1ECE00B72803212C1D010500EDB021361D011000EDB0CD7229010300EDB021E6C213
:081EEC00011800EDB011E5C181
:0B1EF400214A1D011800EDB021FEC2C4
:091EFF00011800EDB0C93AB3C0AE
:121F08003DC0E5CDEE46210100AFED52E1C8D83AB2C1A6
:041F1A002F32B2C1EF
:0A1F1E00B7C82B362023C93A8FC143
:061F28004FB7C83A90C15A
:201F2E00CB5F2804CD1020C979FE1F2004CD1020C9061E213118110600BE28071910FACD75
:0C1F4E001020C93E14B92804AF32B4C101
:201F5A00237EB7CA741F3DCA7C1F3DCA961F3DCAA21F3DCAE71FCD1020C9CDF21F5E235604
:081F7A00EBE9CDF21F3A90C122
:051F8200CBD73290C135
:061F87005E23562196C105
:031F8D00229BC1D3
:041F9000AF32A2C109
:051F9400EBE93A90C1E9
:131F9900CB57C2EA1FCDA422C9CD7822CAEA1FE52190C15B
:091FAC00CB662033CBE62A9BC171
:031FB500119AC1BD
:0E1FB800EBAFED52EB28240E2E7123229BC1BD
:081FC600CD2F2220183AA2C120
:081FCE00B7CC8E213C32A2C108
:031FD6002A9FC17E
:041FD90023229FC15F
:181FDD0079D3FBCDAC21E1C3EA1FC3EA1F2323235E2356EBE93A90C1F3
:071FF500CB97CBA73290C18E
:031FFC003A94C153
:031FFF003293C159
:04200200793294C1DA
:08200600235E2356ED53AEC129
:05200E0023C93A90C156
:06201300CB4FC02190C17B
:08201900CB86CB9EAF328FC1D4
:07202100C9CD1A283AADC138
:09202800B7C8CD6420AF32ADC190
:06203100C93E0132ADC101
:05203700C9AF32A3C196
:04203C003C32ADC1C4
:06204000C93E0132A3C1FC
:0320460032ADC1F7
:04204900C93A95C13A
:03204D003294C109
:07205000CD0622C02190C162
:05205700CBD62196C16B
:03205C00229BC103
:04205F00AF32A2C139
:0A206300C9CDD720CDCF202A9DC1A2
:0C206D00CDC6213E1047CD6D213A95C133
:13207900FE1620070614CDDB21181BFE192014E52A9DC14B
:03208C0011E5C19A
:17208F00AFED52E12007060ACDDB211803CDC621CDE720C93A6BC09A
:0520A600CBBF326BC04E
:0620AB00D3F8C93A6BC036
:0520B100CBFF326BC003
:0620B600D3F8C93A6BC02B
:0520BC00CBB7326BC040
:0620C100D3F8C93A6BC020
:0520C700CBF7326BC0F5
:2020CC00D3F8C93E02D3EBCDD321C93E0CD3EBCDAC21C93E0ED3EBCDAC21C9CDD720CDCFA0
:0420EC00202A9FC146
:0420F000ED5B9DC146
:0920F400AFED52457DB732A1C1E8
:0F20FD00280AFE183803C61047CD6D213AA3C13B
:09210C00B7C4DF20C9AF32A2C143
:032115002A9DC13F
```

```
:11211800CB7E200A233CB7FE3038F5AF18F2229FC197
:0321290032A1C11F
:08212C00C9CD2F22C02A9FC17A
:032134003AA1C10C
:0C213700CD0423233CFE3038072A9DC154
:0D214300CDF922AFCB7E28EF10EA229FC11C
:08215000CDE720C9F52A99C36F
:04215800ED5B97C3E1
:20215C00AFED520604280104CD2D21F1C93E1018023E14D3EBCDAC2110F9C93E20D3FBCD8C
:20217C00AC2110F9C93E0AD3EBC93E01D3EBCDD321C9F5CDD7200605CD77210605CD6921C3
:20219C00CDDF20F1C92B2B2B2BCBFE23232323C9F53E803D20FDF1C93838060E0C01007EFD
:2021BC00B7C8D3EBCDAC212318F506187EE67FD3FBCDAC212310F50608CDAC2110FBC97E71
:1521DC00E67FD3FBCDAC212310F50608CDAC2110FBC93A92C1F0
:0D21F100B7C9CD6E22C8EB7ED63032A0C635
:0521FE0037C93A94C14D
:06220300FE04C93A94C17B
:1E220900FE13C8FE1BC8FE1EC8FE1DC8FE14C8FE1CC8FE16C8FE15C8FE19C02A9DC164
:0322270011E5C1FD
:08222A00AFED52C8C93A95C19D
:0F223200FE13C8FE1BC8FE16C8FE19C02A9DC1A8
:0322410011E5C1E3
:08224400AFED52C8C93AA6C172
:0A224C00FE13C8FE22C8C93A94C16F
:07225600FE1320063AA5C1AA
:14225D00FE01C9FE1EC8FE1DC8FE1CC8FE14C8C9C92A9BC10A
:032271001196C102
:07227400AFED52C93AA5C10C
:13227B00FE01C8FE02C8FE03C8FE0AC8FE0BC8C92119C292
:03228E00229DC1CD
:0C229100E5D10630CD8840C9C51103C35B
:0A229D00010500EDB0C1C92190C198
:1022A700CBDECD1020C9CD4A20CDA422C93A93C197
:2022B700FE04280ACDC92238055E2356EBE9CDAD22C921DA224F7EB72807B923C8232318FC
:2022D700F537C913472C142F3315E4331AFE34162B3519EE351E4C361DC7361B1F371CABDA
:0522F7003E003AA4C105
:0322FC0032A5C147
:0422FF00AF32A6C193
:05230300C9E521A5C1A0
:06230800034E1C93A95C161
:08230E00FE19C21F232A9DC124
:0323160011E5C10D
:0E231900AFED52CA5323FE1BC22F233AA6C1BA
:10232700FE13CA5823C35323FE13C258233AA5C129
:07233700FE0420102A1CC364
:20233E007CB5C24B23CD6E22C25023180DCD6E222803CD4D2B0601CD2D21CDAD22C93A9544
:01235E00C1BD
:14235F00B72805FE19C26B23CD9C35C9FE1BC2C8233AA6C151
:08237300FE13C298243AA5C133
:08237B00FE1FC28C233AE5C2EB
:0D238300B72806CD8D3BC39824AF32E5C2CC
:03239000329BC0BD
:0723930021A51CED5B4DC20A
:11239A00AFED52C2A423CD9437C921180019224DC2D7
:0323AB001183C2D9
:0423AE00ED539DC18D
:0823B200013000EDB021B0C2C2
:1723BA00CBFECD4120CD1121CD0423C39824FE13C29824AF32A8C1CA
:0323D10032A7C16F
:0323D4002A4BC2CF
:1123D70011D51CAFED522006CDC12BC398242A4BC270
:0423E800ED5B99C34D
:1323EC00AFED52C20824210800197E23B6C208242A97C3F7
:0323FF002299C35D
:0B240200CD932BC398243E0432A4C1EC
:05240D003E013292C106
:032412002119C2CB
:07241500CDB227E52A99C3AF
:03241C00224BC28E
:04241F00DD2A99C356
```

```
:07242300CDD654DD2299C360
:03242A002A97C32B
:04242D00ED5B99C307
:08243100AFED5220572A4BC207
:032439002299C322
:06243C00010100211CC398
:03244200111DC3A6
:202445003600EDB0E1CD8240CDA121CD7640CD8240CDA121CD7640CD8240CDA121CD7640E0
:13246500CD8240CDA121CD7640CD8240CDA121AF3292C171
:032478002119C265
:03247B00229DC1DE
:1A247E00CD4120CD1121CDD92BCD6E2AC39824E1CD7927CD4120AF3292C1B2
:07249800CDAD22C93A95C148
:14249F00B72805FE19C2AB24CD9C35C9FE1BC22F253AA6C166
:0824B300FE13C215263AA5C173
:0824BB00FE1FC2CC243AE5C269
:0D24C300B72806CD8D3BC31526AF32E5C20C
:0324D000329BC07C
:0724D30021551BED5B4DC21A
:0C24DA00AFED52C2052521A51C224DC209
:0324E6001183C29D
:0424E900ED539DC151
:0824ED00013000EDB021B0C286
:0D24F500CBFECD4120CD11213E2132A5C1ED
:0C250200C31526EB111700ED52224DC24C
:03250E001183C274
:04251100ED539DC128
:08251500013000EDB021B0C25D
:0B251D00CBFECD4120CD11213AA5C11D
:042528003D32A5C1DA
:0C252C00C31526FE13C21526AF32A8C14D
:0325380032A7C106
:07253B0021D51CED5B4BC232
:0D254200AFED52C2C025110800DD2A99C37B
:04254F00DD224BC27C
:0D255300DD19DD7E00DDB60120F22A4BC24D
:032560002299C3FA
:052563003E013292C1AF
:032568002119C274
:0A256B00CDB227E5010100211CC3D9
:03257500111DC372
:202578003600EDB0E1CD8240CDA121CD7640CD8240CDA121CD7640CD8240CDA121CD7640AC
:13259800CD8240CDA121CD7640CD8240CDA121AF3292C13D
:0325AB002119C231
:0325AE00229DC1AA
:2025B100CD4120CD1121CDD92BCD6E2AC3152621ED1CAFED522006CD932BC315262A97C35E
:0925D100AFED52200AED5399C34D
:0B25DA00CDC12BC315263E013292C17B
:0325E5002A4BC2BC
:0F25E800110800AFED52E5DDE1DDE5DD2299C31D
:0325F7002119C2E5
:0725FA00CDB227DD2A4BC220
:04260100DD2299C37A
:06260500DDE1DD224BC205
:0A260B00CD7927CD4120AF3292C1F6
:20261500CDAD22C93E3918243E3818203E37181C3E3618183E3518143E3418103E33180CC4
:10263500 3E3218083E3118043E3018004F2A9BC11F
:08264500CD532220052196C1AE
:05264D001815119AC1EF
:0D265200EBAFED52EBDAD92620083A90C12B
:0A265F00CB67CAD9267123229BC164
:0A266900CD0622206B06053AA5C13C
:08267300FE11CA9C263A94C135
:11267B00FE1BC28926CD49222054060618133AA5C141
:07268C00FE01200C3A94C18D
:0C269300FE1528053E045F18153AA2C190
:0E269F00B7C5CC8E21C13C5FB8302F2A9FC139
:0426AD0023229FC184
```

```
:0326B10032A2C191
:0326B4003AA1C187
:0426B7003C32A1C14F
:2026BB00CDD72079D3FBCDAC210604CD4922200206057BB838050601CD6921CDDF20CDA4E0
:0726DB0022C93E133295C134
:0F26E200CDAE20CD932BCDA422C93E013292C1A3
:0626F10021D51C224BC2A2
:0326F7001119C2F4
:0826FA00011800EDB01124C22B
:0B270200CD7229010300EDB0112EC2C2
:20270D002B2B2B010300EDB0EBCD69282BCBFE23CD8240CD7728CDA1210606CD8840CD90A2
:0B272D0028CDA121CD7E40AF3292C12B
:06273800C93E013292C10E
:06273E0021ED1C224BC23C
:032744001119C2A6
:20274700011800EDB0EBCDA928CD7640CD0329CDA121CD7640CD1B29CDA121CD7640CD3382
:1127670029CDA121CD7640CDD628CDA121AF3292C198
:08277800C9CDA928E52A99C387
:04278000ED5B97C3B3
:20278400AFED52E12803CDA121CD7640CD0329CDA121CD7640CD1B29CDA121CD7640CD33FB
:2027A40029CDA121CD7640CDD628CDA121C9CDA928CD7640CD0329CD7640CD1B29CD764086
:1627C400CD3329CD7640CDD628C9CDD527CD4120C93E013292C13B
:0427DA00DD2A99C398
:0527DE00DDE52A4BC2FD
:0C27E30011ED1CAFED52200CEB1119C2DF
:0B27EF00011800EDB0EB180E2119C21C
:0427FA00DD2A4BC2C7
:0427FE00DD2299C37C
:09280200CDB227DDE1DD2299C30E
:07280B00CD7927AF3292C125
:05281200C9ED5BA9C146
:0B2817007AB3C9CD1328C8ED53ABC144
:052822003E0132B1C1CE
:032827002A9DC126
:0C282A00CD3728CD322021000022A9C1AA
:20283600C9E501B4420A6F030A6703AFED5228080AB703F2462818ED5950E13E18471AB7AE
:16285600FA602877132305C818F4E67F772305C48840C93A9DC371
:07286C005F1600ED5316C3D7
:07287300CD1440C93A9DC3DA
:03287A0032A0C6C3
:0E287D00E5CD9B54E5DDE1CD0F09ED5318C309
:08288B00E1CDA547C93A9DC348
:0328930032A0C6AA
:0E289600E5CD9B54E5DDE1CD0A09ED531AC3F3
:0928A400E1CDA547C9DD2A99C365
:0928AD000E00CD1A55ED531CC3B9
:2028B600E5EBE511E803AFED52380FD1210000010A00CD0302E1CD1440C9D1E1CD1740C9E3
:0428D600DD2A99C39B
:0928DA000E01CD1A55ED5324C383
:2028E300E5EBE511E803AFED52380FD1210000010A00CD0302E1CD1740C9D1E1CD1B40C9AF
:04290300DD2A99C36D
:092907000E02CD1A55ED531EC35A
:0F291000CD4B2928023E01CD1D40C9DD2A99C3B8
:09291F000E03CD1A55ED5320C33F
:0F292800CD4B2928023E01CD1D40C9DD2A99C3A0
:092937000E04CD1A55ED5322C324
:20294000CD4B2928023E01CD1D40C9E5D521E803AFED52200DD1210000010A00CD0302AF7B
:15296000E1C9D1E1C9CD1A5579FE0120013CCD1D40C93A11C02E
:17297500210510B7C8210B1D3DC8210B1D3DC821051DC9E52A9BC179
:0A298C00CD1914E13FC9DD211EC37F
:032996003AA5C19E
:20299900FE05C2E129DD5E02DD5603D5DD6E04DD660519CDA202EB41E1CDA202CD5703DD64
:1B29B9005E00DD5601D541E521E803AFED52CDA202D1CD4603CDC5022220C38B
:0C29D400D119EB21E803AFED522222C321
:2029E000C9FE062043DD5E04DD5605D5DD6E00DD660119CDA202EB41E1CDA202CD5703DDC0
:1B2A00005E02DD5603D541E521E803AFED52CDA202D1CD4603CDC5022222C33D
:0C2A1B00D119EB21E803AFED52221EC3DD
:202A2700C9FE07C0DD5E00DD5601D5DD6E02DD660319CDA202EB41E1CDA202CD5703DD5EC0
:1A2A470004DD5605D541E521E803AFED52CDA202D1CD4603CDC502221EC355
```

```
:0C2A6100D119EB21E803AFED522220C395
:042A6D00C921A8C112
:072A7100CB86CB8E21A8C12A
:0A2A7800CB96CB9ECBA6C921A8C1C6
:082A8200CB9ECBA6C921A8C11F
:082A8A00CB96CBA6C921A8C11F
:082A9200CB96CB9EC921A8C11F
:062A9A00CB86C921A8C192
:032AA0003AA5C193
:202AA300FE042002CBC6FE082008CBCEFE092002CBCEFE052002CBD6FE062002CBDEFE073B
:152AC3002002CBE6FE0A2002CBEEFE0BC0CBF6C93E010196C15E
:202AD800571EFF210000CD882938317BB7F2F82A0A03FE2E2807CD5A63381718E91C18E6C0
:202AF8007BBAF2022B1C0A0318ECCD8829380D0318F8CD882938030318F837C97CB528330F
:202B18007AB728147BB7F2232B1E007BBAF2302B1C3E30CD5A6318F3E5210000D9E14521D9
:022B3800B8C61D
:1B2B3A00237ED929855F3E008C57292919D910F0D9AFC9CD9D2A1E023AA5C1EF
:192B5500FE08280EFE09280A1DFE043804FE0938011D7BCDD52A3AA5C153
:182B6E00FE02280CFE0A2808FE032804FE0B2004AFCD8363E52114C34A
:032B86003AA5C1AC
:0E2B8900087 5F160019D1732372C9AF32A7C13E
:032B97003A9DC3A1
:032B9A0032A0C6A0
:062B9D00CD9B542297C3FA
:032BA3002299C3B1
:032BA600224BC2FD
:062BA900CDEC262119C24B
:032BAF00229DC1A3
:0B2BB200CD4120CD11213E0132A4C115
:0A2BBD00CDF922C9CD39272119C234
:032BC700229DC18B
:0B2BCA00CD4120CD11213E0532A4C1F9
:082BD500CDF922C9AF32A7C1FE
:052BDD003E0432A4C11A
:072BE200CDF922C92116C341
:042BE9007E329DC3D8
:032BED0032A0C64D
:062BF000CD9B542297C3A7
:032BF6002299C35E
:032BF9002A18C3D4
:032BFC0022AAC644
:052BFF003E20325DC321
:062C0400CD3C572A1AC363
:042C0A00DD2A97C365
:092C0E00CD1F09C93E013292C13B
:032C17003AA8C117
:032C1A00325DC365
:032C1D002A1CC3AB
:032C200022A0C629
:032C23002A24C39D
:032C260022A2C621
:032C290011A4C62D
:032C2C00211EC3A3
:082C2F00010600EDB03A5FC39D
:0F2C37003D2805CD69531803CDD253AF3292C15A
:042C4600C93AA5C121
:202C4A00FE01CA762CFE02CAA82CFE03CAC22CFE04CAE32CFE05CAB32DFE06CACA2EFE0755
:182C6A00CAF22FFE08CA3A31CDAD22C9CD6E222823CD4D2B7B329DC3CD
:032C820032A0C6B7
:062C8500CD9B542297C311
:032C8B002299C3C8
:032C8E00224BC214
:202C9100CDEC26CD41200601CD2D211806CDE62BCDC12BCDAD22C9CD6E222803CD4D2BCD40
:192CB100E62BCDEC26CD41200601CD2D21CDAD22C9CD6E2228123A9DC334
:202CCA00B72009CD1C4DCDB64CC3DF2CCD4D2BCDE62BCDC12BCDAD22C9CD6E22C2F92C2A88
:022CEA001CC309
:082CEC007CB5CAAF2D21A8C17F
:082CF400CBC6C3952D2A1CC3B9
:142CFC007CB5C29C2DCD4D2B0E00CDB154DA322DDD2299C34F
:042D1000ED5B99C31B
:032D14002A97C338
```

```
:0F2D1700AFED522810EB110800AFED52224BC266
:112D2600CDCE27C3952DCDC12BC3AF2D3E01325FC36A
:032D370032A7C1FF
:0F2D3A00CD122CCD1328CA4E2D210000221CC310
:082D49000605C3972D2A97C36C
:042D5100ED5B99C3DA
:162D5500AFED52C2612DCDC12BC3AF2DEB110800AFED52224BC2B1
:052D6B003E013292C19F
:042D7000DD2A99C3FC
:052D7400DDE52299C31A
:032D79002119C25B
:092D7C00CDB227DDE1DD2299C38F
:0D2D8500CDA928CDA121CD7640AF3292C15D
:202D9200CD41200601CD2D211813CD4D2BCD122CCDCE27CD132828EB0605C3972DCDAD224B
:202DB200C9CD6E22CA512ECD4D2B21E803AFED523012CD122CCDCE27CD1328C45421CD75C1
:072DD2002AC3C62E21A8C18F
:082DD9007EE61820622A20C3E7
:042DE100ED5B22C3C1
:082DE500197CB5282F3AA7C1A3
:0B2DED00B72029CD92293E1F32A8C15B
:122DF800CD122CCDCE27CD1328C45421C2C62E2A1EC3FA
:122E0A0011E803AFED522823CD7F2A060118212A1EC3C0
:202E1C0011E803AFED5206012014CD122CCDCE27CD1328C45421C2C62ECD752A0603CD2D3E
:182E3C0021C3C62ECD122CCDCE27CD1328C45421C2C62E18E421A8C15C
:0A2E5400CBD67EE618205D2A1EC3CF
:0D2E5E0011E803AFED52284406013AA7C168
:092E6B00B7CAB22E3E013292C139
:042E7400DD2A99C3F7
:052E7800DDE52A4BC25C
:032E7D002299C3D4
:032E80002119C253
:092E8300CDB227DDE1DD2299C387
:162E8C00CDA928CDA121CD7640CD0329CDA121CD7640AF3292C141
:202EA200CD41200601C3B22ECDCE27CD752A0603CD2D21C3C62ECD122CCDCE27CD13282832
:202EC200E7CD5421CDAD22C9CD6E22CA702FCD4D2B21E803AFED523012CD122CCDCE27CD81
:0E2EE2001328C45421CD752AC3EE2F21A8C198
:082EF0007EE614205C2A1EC3DB
:042EF800ED5B22C3A9
:082EFC00197CB528293AA7C191
:0B2F0400B72023CD92293E1F32A8C148
:0C2F0F00CD122CCDCE27DAEE2F2A20C3E5
:122F1B0011E803AFED522823CD872A060118212A20C3A4
:202F2D0011E803AFED5206012014CD122CCDCE27CD1328C45421C2EE2FCD752A0602CD2D04
:132F4D0021C3EE2FCD122CCDCE27CD1328CA462F2A97C3D8
:042F6000ED5B99C3C9
:0F2F6400AFED520604C24B2F060318DB21A8C1A4
:0A2F7300CBDE7EE61420662A20C3A0
:0D2F7D0011E803AFED52284D06013AA7C13F
:092F8A00B7CADA2F3E013292C1F0
:042F9300DD2A99C3D7
:052F9700DDE52A4BC23C
:032F9C002299C3B4
:032F9F002119C233
:092FA200CDB227DDE1DD2299C367
:1F2FAB00CDA928CDA121CD7640CD8240CDA121CD7640CD1B29CDA121CD7640AF3292C15F
:202FCA00CD41200601C3DA2FCDCE27CD752A0602CD2D21C3EE2FCD122CCDCE27CD132828B8
:202FEA00E7CD5421CDAD22C9CD6E22CA9D30CD4D2B21E803AFED523012CD122CCDCE27CD2A
:0E300A001328C45421CD752AC3363121A8C124
:083018007EE60C20622A1EC3B3
:04302000ED5B20C381
:08302400197CB5282F3AA7C161
:0B302C00B72029CD92293E1F32A8C119
:12303700CD122CCDCE27CD1328CD5421C236312A22C338
:12304900011E803AFED522823CD8F2A060318212A22C369
:20305B0011E803AFED520603200FCD122CCDCE27CD1328C45421C23631CD752A0601CD2D8F
:12307B0021C33631CD122CCDCE27CD132828EA2A97C38D
:04308D00ED5B99C39B
:0F309100AFED520603C27930060218DC21A8C148
:0B30A000CBE67EE60CC228312A22C3DA
:0B30AB0011E803AFED5228673AA7C1FF
```

```
:0730B600B7C2CD302A97C319
:0430BD00ED5B99C36B
:1130C100AFED520603C27930060218AC3E013292C10C
:0430D200DD2A99C397
:0530D600DDE52A4BC2FC
:0330DB002299C374
:0330DE002119C2F3
:0930E100CDB227DDE1DD2299C327
:2030EA00CDA928CDA121CD7640CD8240CDA121CD7640CD8240CDA121CD7640CD3329CDA13D
:08310A0021CD7640AF3292C1E5
:20311200CD41200603C32231CDCE27CD752A0601CD2D21C33631CD122CCDCE27CD132828D9
:16313200E7CD5421CDAD22C9CD6E22CA4331CD4D2B3E1F32A8C121
:14314800CD122CCDCE27CD1328C45421C2B9313E013292C1F5
:03315C002119C274
:07315F00CDB227DD2A99C360
:04316600DD224BC259
:07316A00E5010100211CC377
:03317100111DC36A
:2031740003600EDB0E1CD8240CDA121CD7640CD8240CDA121CD7640CD8240CDA121CD7640A4
:13319400CD8240CDA121CD7640CD8240CDA121AF3292C135
:0331A7002119C229
:0331AA00229DC1A2
:2031AD00CD4120CD1121CDD92BCD6E2ACDAD22C9CD6E22CAD031210E1DCD9922CD4D2BEB0E
:2031CD00CD9C60CD1E32CDAD22C9CD6E22CAE431CD4D2BEBCD1961CD1E32CDAD22C9CD6E27
:0C31ED0022CA1732CD4D2BEBDD21C9C6E4
:0F31F900CD0A09EBAFED52EB28053E0132A4C31E
:04320800DD21C9C635
:07320C00CD1F09ED5B23C09B
:04321300192208C0B4
:0B321700CD1E32CDAD22C9AF32B1C1D7
:19322200CD1328060128020603CD2D21CD561ECDC51ECD3832C92A9DC1BD
:19323B00CDD720CDCF20CDC6213E1047CD6D21CDC621CDE720C93A95C175
:093254005FFE13C271323AA5C1FC
:17325D00FE01CA55330603FE02CAB232FE03CAB232C3BB323AA3C155
:20327400B7CA2B337B0603FE19CAB232FE160601CAB232FE1ECAB232FE1DCAB232FE1CCAD2
:20329400B232FE15CAB232FE1BC2AF32CD4922C2AF32CD1121CDE720C3B532C32B33CD2D46
:0A32B40021CD8E21C32B332A4BC21B
:0432BE00ED5B99C368
:0B32C200AFED520605CAE3323AB4C17A
:0A32CD003DCAF432CDD7202A99C380
:0432D700ED5B97C351
:1232DB00AFED520604280104CD2D21CD8E21AF32A2C1E1
:0432ED003C32B4C1FA
:0632F100C32B332A4BC27F
:0432F700ED5B99C32F
:0E32FB00AFED52CA2B33CD53543E0232B4C154
:04330900AF32A8C176
:04330D00ED5B99C318
:033311002A97C335
:0F331400AFED52280FEB110800AFED52224BC264
:0F332300CDCE271803CDC12BCDAD22C93AA5C100
:0D333200FE01C25133CDF32138033A9DC393
:03333F00329DC3F9
:0333420032A0C6F0
:06334500CD9B542297C34A
:13334B00CD9D5ECD932BCDAD22C9CD8B22217C331131C269
:09335E00010D00EDB0EB3A9DC336
:20336700C63077233E29772323CBFECD4120CD1121CDA422C944656C6574652046696C654D
:05338700020283A95C169
:0E338C00FE15280AFE13C20E343E153295C1FE
:0C339A00CDA320CD8B2221D1331131C2F4
:0933A600010A00EDB0EB3A9DC3F1
:1B33AF00C6307723EB21DB33010900EDB0EBCBFECD4120CD11213E0132A4C1FB
:2033CA00CDF922CDA422C9436F70792046696C652020546F2046696C6520CD6E222822AF4B
:1E33EA00CDD52AEB210B00AFED52D2FD33CDAD22C389332005CD123418077B32A0C66D
:0E340800CD8E5ECDDD26CDAD22C9ED5B97C326
:033416003A9DC319
:1A341900123E68470E133EA0C5CD4634C10D280678C6084718F0AF3297C3C3
:16343300060000E203EA2C5CD4634C10DC878C6084718F12130C323
:11344900772370230608 1A77231310FA3600223CC30F
```

```
:15345A00CD0D3ED5CDA53DD1CD2D3ECD583EC9CD0D3E2130C360
:0D346F003EA077233E6877233600223CC341
:09347C00CDA53DCD0D3E2130C36C
:093485003EA177233600223CC36E
:08348E00CDA53D069821C9C639
:16349600CDE93D7323052805CD463E18F3CD2D3ECD0D3E2130C3A5
:0C34AC003EA27723AF77233600223CC3FA
:0934B800CDA53DCD0D3E2130C330
:0934C1003EA377233600223CC330
:0834CA00CDA53D06002161C7FC
:1334D200CDE93D7323052805CD463E18F3CD2D3E21C9C6E8
:0434E5007E329DC3D3
:0834E900AF77C93E1A3295C10C
:0334F1002AAEC13F
:0334F400229DC155
:1034F700CD3820CDA422C9CDAD22C93E013292C11B
:053507003E163295C1E3
:14350C00CDA320CD8621CD5D35CD4120CD11213E0432A4C142
:07352000CDF922AF3292C188
:0F352700CDA422C9212C1DCD99223E0132B3C162
:20353600CD6E22280A3E01CDD52ACD9E5F1803CDCA5FCD9C35CDAD22C9486F6C64204174A1
:10355600205469 6D652028CD8B22214F351131C24B
:0E356600010E00EDB0EBCDEE463E013292C1FB
:0E357400CDC8463E29772323CBFEAF3292C14D
:0B358200C921221DCD9922AF32B3C138
:08358D00CDFF5F3E183295C12D
:0E359500CD9C35CDAD22C9CDA320AF32B1C142
:0335A3003A95C195
:0635A6005F3E193295C1E1
:0635AC00BB20352A9DC181
:0335B20011E5C15F
:0935B500AFED52282AEB229DC162
:2035BE00CDD720CDCF20CDC6213E1047CD6D21CDC621CD1121CDE720CDDF203E0932A4C198
:0935DE00CDF922C3EA3521B5C183
:0335E700229DC161
:0735EA00CDAD22C93AA5C1D5
:1835F100FE09CABD31FE0ACAD731FE0BCAEB31CDAD22C93E013292C111
:053609003E1E3295C1D8
:0C360E00CDA320CD8B22216A361131C2E1
:09361A00011100EDB0EB3A9EC372
:07362300C63077233AA4C36F
:17362A00B72803362A2336292323CBFECD4120CD11213E0132A4C1B3
:07364100CDF922AF3292C166
:0E364800CDA422C9210E1DCD9922AF32B3C1EF
:20365600CDF3213005CDB15E1803CDC85ECD9C35CDAD22C9496E697469616C697A652046D9
:09367600696C652028AF32B3C174
:05367F003E013292C182
:05368400 3E1D3295C15E
:0C368900CDA320CD8B2221E1361131C2EF
:09369500010C00EDB0EB3A9EC3FC
:07369E00C63077233AA4C3F4
:1736A500B72803362A2336292323CBFECD4120CD11213E0132A4C138
:0736BC00CDF922AF3292C1EB
:2036C300CDA422C921271DCD9922CDF3213005CD135F1803CD255FCD9C35CDAD22C9507515
:1236E3007267652046696C652028CDA3203E1B3295C13E
:0636F50021251B1183C218
:0836FB00013000EDB02183C293
:03370300229DC143
:03370600229FC13E
:0B370900CD4120CD11213E0C32A4C1A7
:07371400CDF922AF32A6C17E
:07371B00CDA422C93AA5C1AB
:20372200FE0CCA9437FE13CAC637FE14CADF37FE15CAF837FE16CAAF38FE17CAC838FE1858
:20374200CA2A39FE19CA383AFE1ACA513AFE1BCA6A3AFE1CCA833AFE1DCA9C3AFE1ECA06AB
:20376200 3BFE1FCA653BFE20CA573CFE21CA703CFE0DCA1E3DFE0ECA223DFE0FCA263DFED8
:1637820010CA2A3DFE11CA2E3DFE12CA5F3ECDAD22C9AF32E5C248
:0637980021551B224DC269
:03379E001183C2D2
:0437A100ED539DC186
:0837A500013000EDB021B0C2BB
```

```
:0D37AD00CBFECD4120CD11213E1332A4C131
:0837BA00CDF9223E1332A6C135
:0737C200CDAD22C93AE5C2BA
:0937C900B7C2D8373E0132E5C257
:1037D200CDDB3CC3DB37CDCA3CCDAD22C93AE5C215
:0937E200B7C2F1373E0132E5C225
:1037EB00CDDB3CC3F437CDCA3CCDAD22C93AE5C2E3
:0937FB00B7C20A383E0132E5C2F2
:10380400CDDB3CC30D38CDCA3CCDAD22C93AE5C2AF
:0A381400B7C23138214F3811B5C298
:04381E00ED539DC108
:0D382200013000EDB0CD38203E0132E5C28E
:06382F00181AAF32E5C2D9
:0738350000217F3811B5C22C
:04383C00ED539DC1EA
:20384000013000EDB0CD3832C3886ECDAD22C9546573742074696D653A202034206D696EC4
:203860007574657320202050726573737320454E544552206B657920746F20626567696E5299
:20388000616D20746573742069622070726F67726573732E202020556E697420696E6F70EA
:1238A000657261626C652E2E2E2E2E776169743AE5C22F
:0938B200B7C2C1383E0132E5C283
:1038BB00CDDB3CC3C438CDCA3CCDAD22C93AE5C241
:0838CB00B7C2F4383C32E5C23B
:0338D3003A8EC06A
:0738D600CDB16FD521B5C291
:1B38DD00CD8E22E1EBCD1440EB21FF38013000EDB0CD3820C3FB38AF32E5C2B2
:2038F800CDCA3CCDAD22C925206F66206C61737420393620379636C657368616420616E3C
:153918006F6D616C6F7573206576656E74732E2020203AE5C276
:0A392D00B7C254392190393A70C036
:09393700B7200321F03911B5C2DB
:04394000ED539DC1E5
:0D394400013000EDB0CD38203E0132E5C26B
:06395100C38C393A70C07E
:07395700B7CA82393A9BC098
:0A395E00FE05CA82393E05329BC007
:053968003EFF329DC08E
:06396D0021C03911B5C2B2
:04397300ED539DC1B2
:0F397700013000EDB0CD3820C38C39AF32E5C23E
:03398600329BC0B1
:20398900CDCA3CCDAD22C9546573742074696D653A2020382063616D206379636C65735081
:2039A9007265737320454E544552206B657920746F20626567696E4368656636B76616C767B
:2039C9006520696E746567726974792020202072756E6E696E672E2E2E2E2E2E2E2E2E2E2D
:2039E9002E2E2E77616974450756D70206D7573742062652072756E6E696E672061742063
:203A09006F6E7374616E7420666F7720726174652E202020204F55544C45542020207E7
:123A290020202020202020202020494E4C4554 3AE5C2EE
:093A3B00B7C24A3A3E0132E5C26D
:103A4400CDDB3CC34D3ACDCA3CCDAD22C93AE5C22B
:093A5400B7C2633A3E0132E5C23B
:103A5D00CDDB3CC3663ACDCA3CCDAD22C93AE5C2F9
:093A6D00B7C27C3A3E0132E5C209
:103A7600CDDB3CC37F3ACDCA3CCDAD22C93AE5C2C7
:093A8600B7C2953A3E0132E5C2D7
:103A8F00CDDB3CC3983ACDCA3CCDAD22C93AE5C295
:113A9F00B72809CD6E22C2C73AC3CF3A3E0132E5C22A
:063AB00021D63A11B5C257
:043AB600ED539DC16E
:203ABA00013000EDB0CD4120CD1121180BCD1C4DCD132820F3CDCA3CCDAD22C9456E7465B9
:203ADA00722066756C6C207363616C65206F757470757428782E787878206D762F76296967
:0F3AFA003A20A020202020202020203AE5C2C2
:0A3B0900B7C2263B21353B11B5C2BF
:043B1300ED539DC110
:0D3B1700013000EDB0CD38203E0132E5C296
:203B2400180BCDB64CCD13282003CDCA3CCDAD22C952656C6561736520737979737465D2086
:203B440070726573737372652E5468656E207072657373204554455220B65792E202069
:043B6400203AE5C25C
:093B6800B7C2773B3E0132E5C211
:0C3B7100CD8D3BC3893BCDB13B3A45C133
:033B7D003246C10C
:133B8000B72003CDFF5FCDCA3CCDAD22C921F73B3A45C162
:063B93002F3C3C3245C14D
```

```
:083B9900280321273C11B5C2ED
:043BA100ED539DC182
:0F3BA500013000EDB0CD4120CD1121C92130C339
:0B3BB4003EA077233E0577233A45C171
:073BBF0077233600223CC30E
:063BC600CD0D3E2130C3CD
:0A3BCC00CDA53DCD2D3EC92144C119
:103BD6007EB72806175FFE8020021E10733A6AC061
:083BE600E60FB3E67F326AC06E
:083BEE00D3F93A77013243C11B
:203BF600C94D6F746F7220537465702F56616C7665204C6573742020536574206465666651
:203C160061756C742073746174653A20CF464620204D6F746F7220537465702F56616C760D
:203C360065205465737420202053657420646566617574207374617465733A20CF4E2020C0
:043C5600203AE5C269
:093C5A00B7C2693C3E0132E5C22B
:103C6300CDDB3CC36C3CCDCA3CCDAD22C93AE5C2E9
:093C7300B7C2933C3E0132E5C2E8
:033C7C0021B5C2AD
:093C7F00CD8E22219A3C11B5C240
:203C8800013000EDB0CD3820C3963CCDCA3CCDAD22C95350383830302056657273696F6EE3
:203CA80020302E3038442020202863292053706563747472612D50687973696373203139F2
:053CC80038362183C223
:033CCD00229DC174
:0A3CD000CD4120CD1121AF32E5C235
:073CDA00C921EE3C11B5C247
:043CE100ED539DC141
:203CE500013000EDB0CD3820C954455354204E4F5420494D504C454D454E5454542020FE
:203D05002020202020202020202020202020202020202020CDAD22C9CDAD227D
:123D2500C9CDAD22C9CDAD22C9CD6E22C26A3D21B5C29B
:033D3700229DC109
:0F3D3A00CD8E2221A03D010500EDB0EB3A44C330
:093D49005F1600CD584021BAC2FA
:0D3D5200CBFECD4120CD11213E2232A4C177
:083D5F00CDF9223E2232A6C17B
:0B3D6700C39C3DAFCDD52A7D3244C384
:093D7200CD5949CDCD492130C3E2
:0B3D7B003EA077233E0077233A44C3AC
:073D860077233600223CC345
:1B3D8D00CD0D3ECDA53DCD2D3ECDED36CDED36CDAD22C9554E49542021230C363
:043DA800ED5B3CC3D0
:133DAC00EBAFED52EBC87ED506085F2FE68057F33A6DC072
:103DBF00CBBFB2D3FACBF7D3FACBB7D3FA326DC0AE
:103DCF00FB7B0710E2D1CDDB3D2318CDF33A6DC05D
:133DDF00CBF7D3FACBB7D3FAFBC9C51E000608F33A6DC0E4
:153DF200CBB7D3FACBF7D3FAFBDBFAE680B3075F10EA3A6DC02E
:113E0700CBB7D3FAC1C9DBFAE680CCDB3DF33A6DC058
:133E1800CBBFD3FACBF7D3FACBFFD3FACBB7D3FA326DC06C
:063E2B00FBC9F33A6DC073
:133E3100CBFFD3FACBF7D3FACBBFD3FACBB7D3FA326DC053
:063E4400FBC9F33A6DC05A
:1E3E4A00CBFFD3FACBF7D3FACBBB7D3FAFBC901E803CD2E12C9CDAD22C93E013292C136
:053E68003E1C3295C173
:0C3E6D00CDA320CD8B2221D13E1131C20B
:093E7900010F00EDB0EB3A9EC30D
:073E8200C63077233AA4C308
:173E8900B72803362A2336292323CBFECD4120CD11213E0132A4C14C
:073EA000CDF922AF3292C1FF
:0E3EA700CDA422C9211D1DCD9922AF32B3C179
:033EB5003AB4C05C
:203EB8003CCA4C36CDF321D2C73ECD2C601803CD775FCD9C35CDAD22C9436F6E74696E75B0
:123ED800652046696C652028211D1DCD9922AF32B3C153
:083EEA00CD645F3E173295C163
:203EF200CD9C35CDAD22C9CD493FCD285BCD505BE7D8CD6C3F171717175F03CD6C3FB377F9
:0C3F12002303C3FC3ECD493FE7222EC331
:0A3F1E0011243FC3E458ED4B2EC3FD
:203F28001E100AE6F01F1F1F1FCD763F77230AE60FCD763F7723362023031DC22A3FC3939E
:203F480040DFCD285BCD6C3F171717176703CD6C3FB46703CD6C3F171717176F03CD6C3F58
:1C3F6800B56F03C90ACB772802C609E60FC9C5FE0A06303804D6090640B0C1C9AC
:0F3F8400F5C5D5DDE5FDE5DD210A40FD21B9C616
:203F93000600DD5E00DD23DD5600DD237AB328210E00AFED5238030C18F81978B12006FD6C
```

```
:203FB3003600201808060179C630FD7700FD2318D17DC630FD7700FD23FD360004FDE5E184
:203FD300FDE1DDE1D1C1F1B7C8FDE5E5FDE1FD360104C547FD7EFFFE2020023E30FD7700AB
:203FF300FD2B10F0FD36002EFD7EFFFE202004FD36FF30C1FDE1C91027E80364000A00000F
:1A40130000AF18063E0118023E02EBCD843F08CDEE212823C5D5E521B9C664
:0B402D003E04BE28032318FA11C5C68C
:09403800010500EDB81321B9C621
:0E404100EB010500EDB0E1D1C108EB11B9C6ED
:1A404F001AFE04C877231318F7AF18063E0118023E02EBCD843FEB11B9C65B
:204069001AFE04C8FE20280277231318F30601180E0602180A0603180606041802060553E68
:2040890020772310FCC9363A23C9360D23C91A77CBBE1323CB7F28F6C9EFD7C9EFCDBA6215
:2040A900C9110900C3C362FD7E093D202DFD3409FD360A40CD0459FD7E0B3D200DCD125915
:2040C9007BB7285B7AB72857180AFE042006FD5E1AFD561BFD731CFD721DFDCB0A6E2804C1
:2040E900CD2D41D8FDCB0A76281CFD360C00CD5E41C0CD6741FD7E0BFD5E1CFD561DCD728C
:0F41090041FD360A80C9FDCB0A7E28132140C331
:0A4118007EFE01F0FD770C2155C377
:204122003600CDA341D8FD360900C9FDCB007E2808AFFD770AFD770CC9FDE5E111130019CD
:1F414200CDBF4D5F1600FD6E11FD6612AFED523FFD7511FD7412D8FD360A40C92155C395
:0F416100CB46C03601C9FD5E1EFD561F21D6C5D7
:06417000D5C9E52A45C394
:0341760022D0C58F
:0341790021D2C58B
:0A417C00732372237723E311D6C5E5
:0F418600AFED527DE177CBBE7EC6064721D0C597
:0B419500AF8E2310FCCE00772236C650
:2041A000C3D84EFEFD373FC0FD360A20FDE5E111130019CDBF4D2A8901FD7511FD741237BE
:1D41C000C911050018081106001803110A00D7F5C5E5FDE5CDEE212806ED53A9C18A
:2041DD001849CD4D6D200BFDCB08FE3E01210000182D1BCB7A281921FCFFAFED523011FD53
:2041FD004E16FD4617CDCF612821137AB31B2003CD625913FD7E15B720113E06210000FDAB
:20421D00730DFD720E114342CDE658FDE1E1C1F1C9F5C5E5FDE5CDB45838F0AFFD7716FDF1
:20423D0077173E0718D9FD5E0DFD560ECD4D6D2008CD9340CD9340180C732372237AB3C8A1
:09425D00137AB31BC8D5117CC310
:20426600060C1A77132310FACD4D6D200411AE42F7D1D5CD1440D1CD8F40CD7A40E501B45D
:20428600420A6F030A6703AFED5228080AB703F2924218ED5950E11AB7FAA7427713231836
:2042A600F6E67F7723C39340204641554CD40500494C4C4547414C205641524941424C45EC
:2042C600204F5220434F4D414EC40600494C4C4547414C20415247554D454ED40A005318
:2042E600594E544415820455252 4FD21900534541243482055 4E535543434553534655CCE8
:204306001A0046494C452046554CCC1B00414C4C2046494C45532055 5345C41D0046494C3A
:20432600452042553D9640041424F525445C42D014D41582050524553 3555 24520455800
:1D434600434545454445C42E014F5620534F4F456454ED431015A45524F2007
:20436300464C4F5720 2154C53201494C4C4547414C20475241449454E542054494E4494C5CC
:2043830033014F564552204752414144494E5420494D204C494D4434014F5645525D
:2043A30020464C4F52204C494D49043501494C4C4547414C20534F4C564554202527D3C9
:2043C30036015 54E534541424C4520464CFD73701554E41424C4520544F205 A4552CF38A3
:2043E3000146554C4205343414C45204F5554204F46 2052414E47C539014D494E205052 44
:204403004553 535552204558434545445C400044E4F2D53595954454D2044495245A6
:2044230043544456C54C04504F5747552204641494C555245205245434F564552D94D0443D6
:1D444300505552204641494C5245AE010052414D 20544553 54205041535345C4023E
:134460000052414D20544553 54204641494C45C43A5FC368
:1C447300B7C28C44CD5646AFCD78463CFE0520F811B146CDA046C332453A51C1A9
:0B448F00B7DD217A012004DD21A0C66A
:10449A00AFCD78463E01CD4545CB4F280E3A51C1A6
:1444AA00B72032DD5E02DD56031827E5DDE5CD56463A5FC3D7
:0B44BE00FE02280FCD4E46ED5BA0C6AD
:2044C900CDE95711F8FFDD19DD23DD23CDBD4EEBDDE1E1CD1B40CD8F403E024FCD4545CBF1
:2044E90057C48546CD8F403E034FCD4545CB5FC48546CD8F403E04CD4545CB672809DD5EBE
:2045090008DD5609CD1740CD8F403E05CD4545CB6FDDE5CD4E46CD0F09DDE12806DD5E0A81
:20452900DD560BCDA547CD8F403E0711BA46CDA0463E08CD6046CDC046C39340CD60463A07
:024549005DC350
:1C454B00C9C4000000CDE3615F1600FD6E05FD660619FD7505FD7406ED5B95C3C1
:20456700AFED52D8AFFD7705FD7706118845217B45C3E458FD7E0CB7C26259214D45C3FDE0
:2045870058CDEE46CDCD14AF01A645080A5F030A570308CDA0463CFE0920F02BC39340C803
:1445A7004609472E47374740474A475C47634768470162C33D
:0445BB00ED436EC39B
:2045BF00CD3C46C8FE05F2D145CD56464FCD8546182111F245D5FE05CAB146FE06CA5C47DF
:1C45DF00FE07CA6347FE08CA6847FE09CA7147D1C39340362C23C3BF450162C366
:0445FB00ED436EC35B
:2045FF00CDEE46CD3C46C8113646D5B7CAC8463DCA09473DCA2E473DCA37473DCA40473D70
:20461F00CD4A473DCA5C473DCA63473DCA68473DCA7147D1C39340362C23C30246ED4B6EB3
:01463F00C3B7
:064640000A03ED436EC306
```

:20464600FEFF2BCA934023C9FD5E03FD56041806FD5E05FD5606D5DDE1C9D511C66387E540
:204666006F260019EBE11A7723131A7723363D23D1C9F54FCD6046CD8546CD8F40F1C9CD9D
:204686001A5579FE010601200104CD4D6D782005CD614037C9CD1D40B7C9F5C5CD60460197
:2046A600AB46C5D5C9CD8F40C1F1C9CD4E46CD0F09C3A547110000C31440FD5E071600C331
:2046C6001440CDEE46CDEE21281BE5D5EB11E803AFED52380ED1210000010A00CD0302E1DB
:1046E600C31440D1E1C31740E5210000ED5BBCC017
:2046F600010A00CD0302E1D5E5EBCDA44ECD1F4EE1D1C9E5CD5208E5CDEE21281611E803C6
:1C471600AFED52380ED1210000010A00CD0302E1C31740D1E1C31B40ED5BCFC0E2
:034732003AD1C0B9
:064735001810ED5BD2C07C
:03473B003AD4C0AD
:06473E001807ED5BD5C079
:034744003AD7C0A1
:07474700C38347DD21C9C651
:09474E00CD0F09180DDD21C9C6CB
:09475700CD0A091804ED5B0AC04B
:06476000C3A5473AA4C303
:05476600018033A9EC398
:0B476B005F1600C31440E5ED5BA5C322
:034776002AA7C3AC
:2047790001E803CD0302E1C31740C5E5EB4FCDC502EBCDEE21281021E803AFED52200811BD
:204799006400E1C1C31440E1C1C31740C5E5EB3E01CD8363EBE1C1C31440FDE53E0321FDBB
:2047B90047CD03483806FD700FCD0B59FDE1C9FDE53E0521F247CD0348D4E447FDE1C9C5ED
:2047D900D53E0511F247CDE658D1C1FD700FD361000FD731AFD721BC9FD5E0FFD561073E5
:1A47F900237223C9FD7E0F7723C94FCDB458D8C5D579EBCDE658D1C1B7C91D
:0348130031D1D8C8
:09481600CFCFCFCFCFAF32AAC340
:0F481F003E20D3FAAF3D20FDDBF8E68032A9C37F
:0B482E00AFD3FACD5D483E013200C060
:20483900FBCDE651CD5C58CD7E64CDC74DCD1013CD8503CD2059CD151ECD251FCD222000A4
:20485900000018DDCD7F48CD314ACD1849CDCD49CD5A4ACD704BCD704CCD8D48CD924DCDC0
:0C487900631D000000C90196032100C06F
:034885001101C05E
:204888003600EDB0C93E40D38F3E57D38F3E00D38F3E57D39F3E00D39FDB9FE68020FADB71
:1C48A8009FE68028FA0600DB9F04E68020F91E0878FE3030071E143E01323EC323
:1948C4003E57D39F7BD39F3E43D3AF3EB7D3BF3E18D3BF21FE4811D0C568
:0E48DD00010A00EDB03E18D35FD37F21D0C595
:2048EB00017F0AEDB3210849015F0AEDB3AFED47ED5EC90484011E025003E105EB180444E3
:10490B00010003C005E030011803C105E83A6AC095
:0B491B00E6FED3F9DBF9E602323FC3F1
:0A492600F601D3F9CD0D3E2130C398
:0D4930003EA077233E0077233600223CC3D3
:09493D00CDA53DCD0D3E2130C396
:094946003EA177233600223CC398
:0D494F00CDA53DCDE93CD2D3E7B3244C3CD
:06495C006F26002247C394
:074962003A8001672245C302
:074969003A8101672249C3F6
:074970003A820167224BC3EC
:2049770000CDC4493E10D35FDBF9CB47CCFD4FCD9549C3A249210B49015F07EDB3C9F33AFD
:024997006AC0F4
:07499900E6FBD3F9326AC00E
:0649A000FBC9F33A6AC0F6
:0549A600F604326AC0B6
:2049AB00D3F9E6FED3F9F601D3F9FBC9E5C5211249015F06EDB3C1E1C9210849015F0AED89
:0549CB00B3C92170C317
:0849D0000624CD88402170C3CC
:0C49D800CDFC49CD154ACD054A217CC319
:1249E400CDFC49365323CD154ACD054A010A001188C354
:0349F6002172C368
:1F49F900EDB0C9ED5B8B0173237223C9362E233A8D0177C97C2F677D2F6F23C93A44C388
:0C4A1800E56F2600AFCD843FE111B9C668
:134A24001AFE04C8FE20280277231318F3AF06A0212DC533
:074A3700772310FC214DC59F
:034A3E00223BC553
:054A41003E80323DC57E
:064A460001800121ADC357
:034A4C0011AEC3E5
:074A4F003600EDB0217DC32C
:034A560022ABC3CD

```
:044A5900C93AA9C3EA
:074A5D00B72061DD21C9C68D
:0B4A6400CDE04A060AC5057832A0C666
:064A6F00CD9B5411C9C6E5
:0F4A7500EB019801EDB0C110EBCD69343A9DC350
:034A8400329EC39C
:034A870032A0C694
:064A8A00CD9B542297C3EE
:034A90002299C3A5
:034A930011C9C680
:0A4A9600EB019801EDB0DD21C9C667
:074AA000CD0A09ED5308C027
:074AA700CD184BAF32A4C390
:064AAE002A520122A5C3FB
:064AB40021000022A7C34F
:044ABA00ED5B49C3A4
:084ABE00C364613E0132B4C083
:064AC600CD184B2A97C336
:034ACC002299C369
:044ACF00ED5B49C38F
:0A4AD300CD6461114C04ED53A9C13C
:204ADD00C32E42DDE5019801DD360000DD230B78B1C2E54ADDE121E803DD7504DD7405DD9F
:1E4AFD00E50631110800DD19DD3602FFDD3603FF10F4DDE12A9600CD2509C93AB4C053
:064B1B003D200C3282C0B7
:064B2100060BED5B4BC327
:084B2700CDC8473EFF32B3C0C8
:034B2F0032B4C0DD
:034B320032B5C0D9
:064B3500212C0122C0C08A
:064B3B002A500122C6C051
:064B410021000022BCC0AF
:034B470022BAC0CF
:034B4A0022BEC0C8
:034B4D002ACBC6AA
:0A4B50000E03CD0209E5ED5B02C083
:0A4B5A00AFED52E12808793279C06E
:044B6400AF3283C029
:034B68002202C066
:044B6B00ED5304C042
:064B6F00C93E0C326DC0CE
:0D4B7500D3FACD7D4CCDA74C3E013288C057
:034B82003289C0B5
:034B8500328AC0B1
:034B8800327AC0BE
:034B8B0032E7C04E
:034B8E00329FC390
:034B910032 4EC0E1
:064B9400210032224CC09A
:064B9A002A12012233C0C3
:064BA0002A16012235C0B7
:064BA600CD0D3E2130C3DD
:0D4BAC003EA077233E0177233600223CC354
:034BB9002130C3E5
:094BBC00CDA53DCD0D3E2130C315
:094BC5003EA177233600223CC317
:034BCE002130C3D0
:114BD100CDA53DCDE93D6BCD463ECDE93D632223C01A
:034BE200220FC0DF
:034BE500220DC0DE
:144BE8007CD3DC7DD3ECD3FCCD463ECDE93D7BD3FE320CC0F5
:0A4BFC00CD463ECDE93D7B3285C079
:0A4C0600CD463ECDE93D7B3246C1AC
:0C4C1000000000CD2D3E2A96002206C0B8
:064C1C002A460122ADC092
:054C22003E06324FC008
:064C27003A40013273C0A7
:0C4C2D00CD02093A56012A5401327EC122
:034C39003281C104
:034C3C003287C1FB
:034C3F00227CC113
```

```
:034C4200227FC10D
:034C45002285C104
:124C4800002A8D003A8F0018062A90003A92002243C011
:034C5A003245C020
:064C5D002AFF002237C00F
:064C63002A01012239C004
:064C69002AA700223BC057
:074C6F00C92A8E012295C342
:044C7600C93A6DC00A
:064C7A00CB47C83A6DC0F3
:094C8000CB87F60CD3FA326DC0AB
:044C8900F33A6AC0D0
:074C8D00E6F5F60A326AC0E9
:0B4C9400D3F93E53D3AFFBC93A6DC00B
:074C9F00CBC7D3FA326DC050
:054CA600C9F33A6AC0E9
:094CAB00E68FCBFFD3F9326AC099
:204CB400FBC9CDFF5F1100007AD3DC7BD3ECD3FC014003CD2E12DBF90E20E620A94F7AD310
:204CD400DC7BD3ECD3FC3E053D20FD1321D007AFED52382DDBF9E620A9C2D24CED5323C05A
:034CF4002130C3A9
:114CF7003EA077233E017723732372233600223CC3D9
:064D0800CD0D3E2130C379
:0D4D0E00CDA53DCD2D3EC92AD24322A9C11D
:204D1B00C921E803CDA202E541C53E03CDD52AC1D1CDA202CD5703ED5B9C003A9E0047CD40
:204D3B00460341EB0E01210040CD57030601110040CD3C03E5C52A9A00CDA20259C1414B63
:134D5B00D1CD4603CDC5027CB72809ED5BE243ED53A9C14F
:084D6E00C97DD3FE5F2130C3B3
:0F4D76003EA077233E03772373233600223CC3EE
:064D8500CD0D3E2130C3FC
:0A4D8B00CDA53DCD2D3EC93AAAC3C7
:084D9500B7C86F260022A9C176
:0B4D9D00CDB458FD360006ED5B47C3A7
:094DA800CD0B59CD19593AAAC3EB
:0B4DB1003D066628020667ED5B47C365
:064DBC00C3D3723A94C358
:084DC200477E9070C93AB3C0AE
:054DCA003DC02ABCC041
:074DCF00CD1F4EDD21C9C616
:0A4DD6003030CD3E5820283A9EC32D
:164DE0003C4FFE0A2002AF4FCD9465E5DDE1CD3E58280B3A9FC36F
:034DF60032A0C622
:094DF900CD2C6018077932A0C628
:094E0200C32C60C3184B2ABAC08E
:0E4E0B00CD1F4ED0CD3E58C821000022BAC0A7
:054E19003EFF32B5C0B0
:094E1E00C97CB52019E521C9C6C3
:034E2700229BC308
:064E2A0021000022C4C0BB
:034E300022C2C0DB
:034E330022C8C0D2
:034E360022CAC0CD
:134E3900E1AFC9E5EB210000010A00CD030213DD21C9C69F
:204E4C00CDE9571BF501F8FFDD09F13012E1F5DD5E00DD5601D5EBCDA44ED1F1E5DD09F5D2
:054E6C00EBDD229BC3F9
:0F4E7100DD5E00DD5601AFED52CDA44E22C2C072
:094E8000CDAD4ECDA44E22C4C0FC
:0E4E8900DD23DD23DD23DD23CDAD4E22C8C0A9
:0A4E9700DD23DD23CDAD4E22CAC09D
:204EA100F1E1C9D529545D292919D1C9DD5E00DD5601DD6E08DD6609AFED52C9DDE5D51135
:1C4EC100F8FFDD6E00DD6601237CB52004DD1918F12BD1DDE1C9B63E013240C32B
:164EDD00CD714F2009F3CD8D4F2003CDFD4FFBC9CDE04F3A40C334
:134EF3003DFA1C4FFBCD714F201FF3CD8D4F20193A40C331
:074F0600FE02201221D5C5B7
:094F0D00CB7E200BCBFE2A36C638
:0F4F1600E7EC680CE0077FBC9F5C5D5E53A42C30C
:064F2500B7283F3A4DC31E
:204F2B00B7200F3E10D35FDBF9E6022826CDE04F182AFE0120213E10D35FDBF9E602281301
:064F4B00CDE04F3AD0C595
:034F5100324FC319
:084F5400CD06503E01324DC3B1
```

```
:054F5C001809214DC3FE
:164F610034CD3C501803CDB850E1D1C1F1FBED4D2A83013AD4C5A3
:1A4F7700FE0520032A85013E10D35FDBF9E601C02B7CB520F2C9F33A6AC0C1
:0B4F9100E6FED3F9F601D3F9326AC046
:164F9C00FB3E30D35FDB4F3E10D35FDBF9E601C0CDB7493AD0C5A3
:074FB200D34F3E013242C360
:044FB9003D324DC375
:034FBD0021D0C53B
:034FC0002234C6D2
:064FC300CDCD4F3AD1C52F
:094FC900D34FAFC93E013250C3C1
:034FD2002AD2C51B
:0A4FD5007DB7C87CB7C8AF3250C3E7
:054FDF00C9AF3242C31E
:034FE400324DC388
:034FE700324FC383
:034FEA003253C37C
:034FED002A3BC597
:034FF00022CEC509
:054FF300DB4F3A56C33C
:054FF800B7C03241C307
:0D4FFD00210B49015F0BEDB3C9F53A41C32B
:06500A00B7202D2153C365
:04501000343A3DC52C
:06501400BE381B3A2DC559
:07501A00CD8D52473A2EC56F
:08502100B8280EF1ED4BCEC5DD
:0850290002CD7C52ED43CEC51F
:06503100C93E013241C33B
:035037003256C32B
:05503A00F1C92A36C691
:07503F00CD0D4AEB2A34C637
:0950460019381FDB4FEB2A34C6B8
:06504F00BE28062143C348
:0750550034184723223A4C682
:11505C00137AB3C8CDB749237ED34FC97CB52140C38D
:05506D0020133A50C3BE
:06507200B720272A34C616
:04507800232234C6F5
:20507C00DB4FCDA250C9DB4FFE062814FE05280DFE042806FE03C036FCC936FDC936FEC9DB
:0D509C003600C9CD8C493A8701573A40C310
:0850A900BAF2B2503C3240C3E0
:0650B100C93EFF3240C3BE
:1250B700C93E01D35FDB5FE640C2A951DB4F5F3A4DC3BE
:0950C900FE06F232513C324DC3E7
:1650D200FE03F2DF507BB7CAA951C34051FE04F2FE50AF3250C326
:0950E8007BB720083E013250C3E1
:0650F100C345513A45C31E
:0F50F700BBC2A951C34551FE05F221513A50C326
:0C510600B720377BB720073E023250C3B1
:05511200182C3A46C311
:08511700BBC2A951AF3250C325
:10511F00181FFE06F229517B18177BE67F324EC30C
:06512F007B180E3A4EC38E
:0A513500B72817FA93513D324EC31C
:09513F007BD5CD0650D13A4FC3D7
:0651480083CE00324FC3CC
:06514E00C93EFF324EC312
:035154003A4FC30C
:06515700BB28092154C32E
:09515D003420493518463A50C3CC
:09516600B720393A87013251C328
:05516F0006063A41C3F1
:09517400B728020604F33A6AC0F0
:0B517D00E6FED3F9F601D3F9326AC058
:08518800FBCDB749783252C398
:06519000D34FC93A52C3DF
:0751960047BB28082151C3AB
:08519D003520D918073A41C37F
:0E51A500B7CCBB513E30D35FCD8C493A41C3ED
```

```
:0751B300FE01C8AF3241C349
:0451BA00C93A2DC5FC
:0651BE00CD8D52322DC51B
:0751C4008716005F212DC5D5
:0551CB0019EB2A3BC5B1
:0751D000EB7323722ACEC528
:0351D700223BC5B3
:0351DA003A53C382
:0451DD00473A3DC54B
:0451E10090323DC506
:0751E500C9CD10523A56C378
:0951EC00B7C83A8801473A3DC5F5
:0551F500B8D83A2DC5F9
:0751FA00CD8D52473A2EC58E
:0E520100B8C80601110000CDB347AF3256C346
:04520F00C93A57C37E
:05521300B7C03A2DC5F3
:04521800473A2EC51E
:08521C00B8C8CD8D52322EC539
:07522400087160O5F212DC574
:08522B00194E23460A3258C354
:07523300CD7C520A3259C381
:07523A00CD7C520A325AC379
:07524100CD7C520A325BC371
:10524800CD7C520AE67F2828575FCD7C522138C68C
:03525800229CC6CF
:0C525B000A77CD7C52231D20F7229EC64E
:055267003E013257C3B7
:04526C00F33A3DC50F
:06527000C60582323DC5B7
:0C527600FBC9D75718F0F5E50321CDC5A2
:08528200CD19143803014DC5DC
:20528A00E1F1C93CFE07F83E01C901A45209CB520ACE520BD2520CD652000608FD21ADC3E2
:1052AA00FD7E09B72813FD7E0CFEFD200C3A58C37B
:2052BA00FDBE1C2004FD360A40113000FD1910E0C9AF180A3EFF18063EFD18023EFC32401F
:0152DA00C310
:0752DB00C9CD9B5411C9C6A7
:0852E2000198O1EDB02AD1C6CC
:0C52EA007CB53E0120192A780122D1C6B3
:0652F60021FFFF22D3C6D8
:0352FC002ACDC6F2
:0352FF0022D5C6EF
:035302002ACFC6E9
:0353050022D7C6E6
:04530800AF32B7C049
:09530C00C9CD9B54E5ED5B97C38C
:0A531500EB019801EDB0E12297C30F
:03531F002299C30D
:09532200C39854CD9B542297C39B
:03532B002299C301
:07532E00C39854DD2A99C366
:07533500CDD654DD2299C31F
:08533C00C39854060621AAC61D
:035344003A5DC30C
:19534700070707380528 2B10F9C905485E2356EFCDB1543807DD2299C354
:20536000C39854111900C3CE41CD69553861CDB055385CCDEF553857CD1456B7281E3D20C7
:085380002B113501ED53A9C109
:1A538800CDCF411842CD7156CD8556CDA556CD3C57C35857CD8D533A5EC3F6
:0F53A20047EFCB40C27C6DC398543E02325FC3CD
:0953B100CD7156C298543A5DC357
:0553BA00F601325DC3A5
:0453BF00DD2A99C387
:0953C300DD6E00DD660122A0C6CA
:1253CC00C39854C3A240CDCD55CA38540E00ED5BA0C67A
:0953DE00CDB154381ADD2299C347
:0553E7003E02325FC32D
:1553EC00CDEF553860CD1456B7283E3D2847C39854DD2A97C3F3
:0C540100CD4C58280C111A00ED53A9C125
:12540D00CDCF41183ECDB0553824CDEF5538353A5DC354
:20541F00E61C280CCD14563D28183C2806C39854CD7557CDCF57CD8D53EF185DEFCD786138
:09543F001810113501ED53A9C14B
```

```
:0E544800CDCF41CD78611801EFD7C93A5FC3CF
:20545600B7F5EFF1203CCD136B201AD5DDE1AFDD7702DD7703DD3604E8DD360503DD770666
:1D547600DD7707181D210800194E237EB12010AF1213121BEB110800ED522299C3B5
:0B5493001803CD9A57C36B6121C9C6F6
:03549E003AA0C66B
:0554A1003CC82161C8B8
:0F54A6003DB7C8471198011910FDC9DD2A99C3F8
:1554B500CDD654EBCD1A55EBAFED522810D5DDE5E1ED5B99C397
:1854CA00AFED52D120E51802AFC937C9D5DD7E08DDB60920343A51C100
:0754E200B72806AF3251C1EB
:0554E90018223A5DC32A
:0A54EE00E601201BDDE5DD2A97C36F
:0C54F800CD3E58DDE1200E3E013251C1D6
:045504003C325FC313
:03550800325DC34E
:06550B00180BDD2A97C316
:2055110018805110800DD19D1C979B72007DD5E00DD5601C9FE01200FE5DDE5DD23DD23CD83
:20553100BD4EEBDDE1E1C9FE022007DD5E04DD5605C9FE032007DD5E06DD5607C9FE04C067
:1B555100E5DD5E04DD5605DD6E06DD660719EB21E803AFED52EBE1C93A5DC35B
:07556C00E601C8ED4BA0C6EB
:04557300ED5B99C390
:035577002A97C3AD
:0E557A00AFED52200578B12021C9DD2A99C37A
:20558800DD6EF8DD66F923CD19143810DD6E08DD66097CB5C8CD19143002AFC9113201EDB2
:0355A80053A9C143
:0855AB00CDCF4137C93A5DC3C1
:0755B300E601C8ED5BA0C694
:0E55BA002A7801AFED52D0113301ED53A9C193
:0955C800CDCF4137C9ED5BA0C64F
:1455D1002A7C01AFED5228082A7A01AFED52C03DDD2A97C310
:0D55E5001192010DD19DD7700AFC93A5DC3F9
:0655F200E602C82AA2C671
:1255F800ED5B3401CD7B633802AFC9113401ED53A9C1D7
:06560A00CDCF41215DC37C
:0A561000CB8E37C9CD4E563A5DC36C
:20561A00E61CC821E803FE1C281BFE0C2811FE14280DFE182809AFED52C8380D3EFFC9AFBC
:0C563A00ED52D01804AFED52C83A5DC329
:05564600E6E3325DC344
:09564B003E01C911000003A5DC3E3
:0956540047E6042804ED5BA4C63E
:08565D0078E60828052AA6C61C
:0956650019EB78E610C82AA8C66A
:06566E0019EBC93A5DC30F
:07567400E601C8DD2A99C31D
:03567B002AA0C69C
:0A567E00DD7500DD7401C93A5DC35B
:07568800E602200B3A5FC3AC
:0B568F00FE01C021FFFF18032AA2C685
:04569A00DD2A99C3A9
:0A569E00DD7502DD7403C93A5DC337
:0756A800E61CC8DD2A99C3CE
:2056AF00FE042011DD3604E8DD360503DD360600DD360700C9FE082011DD360400DD36052C
:1156CF0000DD3606E8DD360703C9FE0C20132AA4C612
:0956E000DD7504DD74052AA6C67F
:2056E900DD7506DD7407C9FE10200EAFDD7704DD7705DD7706DD7707C9FE1420192AA4C62F
:20570900DD7504DD7405CD4E5621E803AFED52DD7506DD7407C9FE1820BACD4E5621E80383
:0C572900AFED52DD7504DD74052AA6C644
:0A573500DD7506DD7407C93A5DC397
:06573F00E620C82AAAC6FC
:0F574500ED4B9600CD191430026069DD2A97C331
:07575400CD2509C93A5EC32F
:07575B00CB47C8ED4BAEC6C1
:0F576200CBB811E803210000CD9601ED53A5C38C
:0357710022A7C3A9
:05577400C9DD2A97C306
:04577900ED5BA0C67E
:0C577D00CDE957DD6EFCDD66FD22A4C600
:09578900DD6EFEDD66FF22A6C6FE
:03579200215DC3D3
:0D5795007EF60C77C9DDE5FDE5FD2A99C320
```

```
:0457A200DD2A99C3A0
:2057A600110800DD190608DD7E00FD7700DD23FD2310F4DD5E00DD7E01B320E9FD3600004D
:0D57C600FD360100FDE1DDE1C9DD2A97C3DC
:0457D300ED5BA0C624
:0957D700CDE9573005DD2299C32C
:0557E000C9DD2299C3A0
:2057E500CD0258C9010800DD09DD6E00DD66017CB52808AFED52D0DD0918EE37C9DDE5FD6C
:05580500E5DD2A99C356
:20580A00110800DD19DD6E00DD7E01B520F5DDE5FDE1FD190608DD2BFD2BDD7E00FD77003B
:09582A0010F4DDE5E1ED5B99C32A
:20583300AFED5220E6FDE1DDE1C94DDDE5119201DD19DD7E00DDE13CC9DDE5118801DD19E3
:0C585300DD7E00DDB601DDE1C93A57C37F
:06585F00B7C85F3A5BC30D
:15586500FE02D2DA5AFE01CA495A1CC8CDB458D83EFF3257C39E
:08587A00FD360002ED5B58C38E
:06588200CD0B592A9CC663
:125888007EFD7718237EFD7719237EFD771423229CC606
:03589A003A5AC3B4
:20589D00FD77157EFE1BCA8262C38859D7110000CDCF41CD6259C9F5C5D5E50608FD21AD16
:0158BD00C327
:2058BE00FD7E00FD4E09B1280D113000FD1910F0E1D1C1F137C9FDE5E10630AF772310FC0C
:2058DE00E1D1C1F1B7C93E01FD360901FD770BCDF6587CB5C8C3FD58FD731EFD721FC9FDBD
:2058FE007501FD7402C9FD5E16FD5617C9FD7316FD7217C9FD5E18FD5619C9FD7318FD72C0
:08591E0019C90608FD2AABC3FC
:0B592600113000FD19FDE5E1112DC559
:09593100AFED522004FD21ADC3CD
:04593A00FD22ABC3DC
:20593B7C2B040FD7E00E67F200310D8C93D282F3DCAEE593D28283D280B3D2864
:20595E00083D2814FD360000C9FDCB007E2814116400CDCF41C36259FDCB007EFDCB00BE8E
:0D597E00C2A672FD6E01FD6602E92A9CC6FC
:20598B00444DCD285BCD465B38500A77FE222005CD395B3845E5C50E80115F5BE1E51AB7E7
:2059AB00282413FAC059BE2328F41AB7281813F2B5590C18E7E67FBE2805FE2020F42B7918
:1D59CB00E3C1E1771802C1E10323FE8E20B42B0AFE0D28AECD465B0330F5229EC64F
:2059E80011FFFFC3CF41DFCD465B300521A9581848CD505B30030318EE0AB75F217A5DFAF3
:205A0800135AFD7E143D2833C3415AFD7E143D200D21915C7EB72823BB28032318F60321CA
:205A28003B5C7B875F160019EB218F5CAFED5221B3583805EB5E2356EBE7E9110004C3CEC6
:045A4800413A47C1D7
:0B5A4C00B72821FDE50608FD21ADC3D1
:0B5A5700CD4D6D200BCD12592A58C315
:195A6200AFED52280B113000FD1910E9FDE1D7C9CD785AFDE1C92A9CC66A
:205A7B00444D1E03CD285BCD465BD80AFE1B200B116400D7EFCD6259C3CE41FE172003C3E5
:205A9B00FF6CFE4E20043E041831FE5920043E051829FE5820043E071821FE4420021E0606
:1E5ABB00FE0D28030318BDE5ED423E02280CE1AF0BED427B28053E031801E13247C150
:205AD900C9F5DFCD465B3007F1D721275B183DF1FE032006DD2194521818FE042006DD2159
:205AF900A064180EFE0520E1030AB70B20DBDD21F3630A5F03DD7E00B728CEBBDD232806E4
:205B1900DD23DD2318EFDD6E00DD6601E7E9C90AFE20C00318F9CD505B38030318F8E7C9CB
:115B39000323CD465BD80A77FE22C818F3E52A9EC608
:205B4A00CD1914E13FC9CD465BD80AE67FFE0D200237C9AFC9454449D44C494EC5534541D7
:205B6A005243C84348414E47C54C45D453544F52C5494E49D450555247C553544152D44819
:205B8A004F4CC453544FD0434F4E54494E55C5245C6BA5245CD4143434550D450524C490F
:205BAA004EC5494E534552D44454C4554C5345D4535441544C45D4535441544C45C4534F
:205BCA0054415455D3454E5354415455D3444941474C45C4544553D44142444941C74142EE
:205BEA00544553D49B5052494ED450524D4554484FC4505246494CC546494CC55245504F38
:205C0A0052D444449414C4FC745524153C553504655CE525445054524494ED4A150524143545505
:1D5C2A0041CC494E4A4543D4504545CB504F4BC5009B5CF25CFD5C4A5D7A5D845EC1
:205C4700A85E0A5F605F935FF65F1B604460B358B358B3586B61645E7A5E6C60A261A26150
:205C6700AC675862A16DA16DA672A672826201622E652A65606507654468975E676D06628D
:1F5C870001620662556217 3FF93E86888A969E9FA0A2A800CDA54030410601DD21F9C9B0
:205CA600DD5E02DD7E03B32009DD5E08DD7E09B3281F78B72006111B00C3CE410478FE0AEF
:085CC60020080600DD2161C881
:0D5CCE0018D6119801DD1918CFAF3251C161
:045CDB007832A0C6B5
:0A5CDF00180BCDAA40D8AF3251C116
:035CE9003AA0C618
:035CEC00329DC323
:195CEF00C32553EF110000CDC362D8C33153EFDFCD9E63DAC1413A5CC37F
:165D0800FE05F2C141CD285B0AFE3DC2CB4103E721DD633A5CC387
:0F5D1E005F1600197ECDDF62DAC641E521A0C60F
:035D2D003A5CC31A
:0F5D3000087 5F160019D173237221E8633A5CC3B1
:085D3F005F1600197E325DC3FE
```

```
:0E5D4700C33F53EFDFCD9E63DAC1413A5CC328
:1D5D5500B728060B0BE7C37A5DCD285B0AFE3DC2CB4103E7CDDD62DAC64122A0C6F3
:055D72003E01325DC39B
:205D7700C36953DFCD9E633007110500EFC3CE41CD285B0AFE3D2805110A0018EF03E721E3
:055D9700DD633A5CC36E
:125D9C005F1600197ECDDF62300511060018D83A5CC346
:0F5DAE00FE072841FE08283DFE09200A22AEC646
:055DBD003E01325EC34F
:145DC200182FFE0A282BFE05FAD25D3E00CD8363E521A0C6A2
:035DD6003A5CC371
:0F5DD900875F160019D173237221E8633A5CC308
:075DE8005F1600193A5DC3CC
:045DEF00B6325DC3A8
:035DF3003A5CC354
:065DF600B728393A5FC333
:205DFC00B72038CD4F5E382ADF030A03FE842809FE832805B70BFA2E5ECD9E633E02DA8399
:045E1C005D3A5CC3CC
:175E2000B70B0BE7C27B5D0B0AFE83280103E7C369533E01325FC362
:205E3700CD4F5E3810DF030A03E7FE84CA7B5D0BE7B7F27B5DC3D253DF0AFE8D200D03CDC3
:165E5700465B38070AFE0D2802AFC937C9DFCD9E6338063A5CC35A
:205E6D00B72804EFC3C1410B0BE7C37A5D110000CDC362D8C35354CDA540DA6B61CDAA4093
:045E8D00D83AA0C699
:035E9100329DC37C
:0D5E9400C30D53CDA540D2C641DD2A97C3F2
:045EA100DD2299C3A2
:105EA500C3E04ACDA540381BCDAA40D8AF32A4C324
:035EB500219EC368
:045EB800463AA0C600
:095EBC0077B828053E033279C0D5
:155EC500CDDC52CDD45ECDED61CD825FC3F95ECD184B3A9EC320
:035EDA00329FC331
:045EDD00DD21C9C634
:065EE100CD0F092A23C0C9
:045EE700192206C0B6
:065EEB00CD0A092A23C0C4
:045EF100192208C0AA
:075EF500CD4D60C921CBC6B1
:0B5EFC007E23B6C0113101ED53A9C197
:105F0700C32E42CDA5403816CDAA40D8AF32A4C380
:035F17003AA0C6E7
:035F1A00329EC3F1
:0B5F1D00CDDC52CD184B180D3AB3C07C
:075F28003D2007AF32B3C0BA
:035F2F0032B5C0C8
:045F3200DD21C9C6DE
:085F3600CD0F09EBED5B23C068
:045F3E00192206C05E
:0B5F4200ED4BA500CDD509AF327BC0B0
:085F4D00CDED613E033279C085
:045F55003D3271C0A8
:035F59003270C0E3
:0E5F5C00CDB920C9EFCD2F5B21000022B8C0C7
:035F6A003AB3C087
:075F6D003C20043C32B6C0E9
:085F7400CDED613E0132B4C025
:035F7C0032B3C07D
:035F7F0032B5C078
:035F82003A70C0B2
:0A5F8500FE023E01CA55613271C0F0
:035F8F003270C0AD
:1A5F9200C9CDA5403832CDDD62DAC6417CB52005CD184B183F3E0132B4C061
:165FAC00ED5B7801EBE5AFED52E13801EBCDA44ECD1F4E22BAC0C6
:035FC20022BCC03E
```

:035FC50022BEC039
:055FC800180F3AB3C000
:095FCD003C2003D718202ABCC0B7
:035FD60022BAC02C
:045FD900AF32B3C070
:035FDD0032B5C01A
:065FE00021000022B8C000
:035FE6003A70C04E
:075FE900B720073C3271C034
:035FF0003270C04C
:105FF300C3ED61EFCDCC612803CDED61AF32B3C00A
:0360030032B5C0F3
:036006003271C034
:036009003270C032
:03600C003A46C150
:05600F003DC03246C156
:0B601400CD7D4CCDA74CC9EF3AB4C0C5
:10601F003CCAA85ECDBA623819CDAA40D83AA0C6FC
:03602F00329EC3DB
:04603200AF32A4C322
:17603600CDDC52CD3E582003C3775FC3745FEFCDED613E033279C0ED
:04604D00AF3286C028
:036051003287C0D3
:09605400CDB920CDF7083A70C067
:08605D00B7C821181D1103C38F
:126065000104000EDB0C934EFDFCD9E63DAC1413A5CC3B9
:17607700FE012805FE05C2C141CD285B0AFE3DC2CB4103E73A5CC379
:1E608E00FE01C20B61EF3E02CDDF62DAC641ED5B3401CD7B63300A113401ED53A9C157
:0760AC00C3CE41E52ABCC090
:0760B300CD1F4EDD2A9BC347
:1360BA00E1EBDD6E02DD6603AFED52EB28053E0132A4C396
:0960CD00DD7502DD74033A70C0B8
:0760D6003D2019ED5B02C043
:0460DD00ED5304C0BB
:0760E1007AB3280D3A4FC00D
:0860E8003C20073E023279C0A2
:0E60F0001813E53E01CD5561E13E033279C043
:0460FE00AF3283C07A
:06610200CD02092202C0DB
:20610800C3ED61EF3E00CDDF62DAC6413E00CD8363ED4B9600CD191430026069EBD5DD21D8
:02612800C9C6E6
:10612A00CD0F09EBD1AFED52EB28053E0132A4C3E6
:04613A00DD21C9C6D4
:07613E00CD2509ED5B23C034
:04614500192206C055
:06614900CDED613A70C0CB
:09614F00FE02CC325FC93271C0BE
:056158003EFF3270C0A3
:06615D002A41012274C07A
:20616300C9CDB458D8CD1959CD4D6DC8CD8761117044C3E458CD4D6DC8FDE5CD1259CD6401
:08618300061FDE1C9DED5B97C36A
:0A618B00FD7303FD7204ED5B99C380
:09619500FD7305FD72063A9DC37D
:19619E00FD7707C9EFCDCC61C2ED61CDD661D8FD360003CDE3612A95C306
:1B61B700FD7505FD7406214D45C3FD58FD4E16FD4617C31259CDC3612A49C304
:2061D200AFED42C9CDB458D8FD7116FD7017C31959FDE5E111030019C3BF4DC9FDE5CDC31E
:1261F20061CDD6613806118845CDE458FDE1C93A9DC3D0
:0A62040018023EFFFD77072162C378
:03620E00226EC33A
:0D621100DFCD285BCD9E63DAC1412A6EC34C
:03621E003A5CC324
:0A622100FE0ACAC1417723226EC3B2
:14622B00CD285BFE2C200403CD285BCD505B30D7E72A6EC3AD
:20623F0036FFFD7E073C2808CD876111B845180311F845C3E458C32F5BEFFDE5CD045906A3
:05625F0008FD21ADC3A4
:20626400FD7E00FE03200BEBCD0459EBAFED52CC6259D5113000FD19D110E5FDE1C9EFFD79
:07628400E50608FD21ADC392
:0E628B00FD7E00FE04FAA262CD04592A58C31B
:1A629900AFED522004FDCB00FE113000FD1910E2FDE1D7C36259AF325FC394
:0362B300325DC396
:0362B600325EC392

:2062B900C9DFCD285BCD505BE7C9D5AFCDDF62D13008110600CDCE4137C9CD7B6338F3221F
:0262D900A0C65D
:2062DB00AFC93E01DF571EFF210000CD285BCD505B38327BB7F203630A03FE2E2807CD5A2D
:2062FB0063381718E61C18E37BBAF20D631C0A0318ECCD505B380E0318F8CD505B38030371
:20631B0018F8E737C9E77CB528337AB728147BB7F230631E007BBAF23D631C3E30CD5A63DB
:0C633B0018F3E5210000D9E14521B8C6A7
:20634700237ED929855F3E008C57292919D910F0D9AFC9D630F5FA7863FE0AF278637DFED9
:0A63670005F27863F1D5E511B9C61F
:1A6371001977E1D123AFC9F137C9D5EBAFED52EBD1C9F5CDA202ED5B43C060
:03638B003A45C0D0
:20638E0047F1B72005CD46031803CD5703C3C502606911C6630E001AB72817BE13232004C0
:0D63AE001ABE28050C132B18EE79325CC3C3
:2063BB0023444DAFC92323444D37C95449464C504150425043505550524D46464950565378
:2063DB005000010201010100000000010101020408102040800000000500640732640C3BFE
:0C63FB00640F486000110000ED4B02C070
:0764070078B128163AB7C076
:0D640E00B72810210500CDD30EED5BA5C30E
:03641B002AA7C3EA
:07641E00CD0302ED53B8C0ED
:036425003AB3C0C7
:076428003C20043C32B6C029
:09642F00C3775FCDFF5F3282C02C
:07643800C3184BAF32A4C3EF
:04643F003C3282C0A9
:036443002A9CC6CA
:05644600237E32A0C618
:03644B00219EC3CC
:04644E00463AA0C664
:0964520077B828053E033279C039
:0C645B00CDDC52CDD45ECD825F21CBC6DB
:0B6467007E23B6C0113101ED53A9C126
:07647200CD2E42ED5B4BC390
:0F6479000607C3C847DBFA4FCB5720103A60C362
:0D648800CB572809CD775F21000022B8C056
:04649500793260C335
:0F649900CB47CCFF5FC90001A46400AF3257C3EB
:0364A8002170C39D
:0864AB00CDD864280F217CC349
:0864B300CDD86428072188C33D
:1264BB00CDD864C0CDB458D8FD750FFD7410ED5B58C3F0
:1164CD00CD0B593E0411E864C3E658E5060C1139C6E6
:2064DE001ABE2004132310F8E1C9360223FD5E0FFD5610EB010C00EDB0EB36002336002360
:2064FE003600233A80017723C9CDA240FD360004211465C3FD58111D6521AA58C3E45811A9
:20651E002566F7CD154ACD9340C393401E0018021E01CD9B65D811E365213C6518211148D0
:20653E00661811FDCB087E2805CDBF66300BFD34081185662141651806611676721AA58C327
:20655E00E4581E00CD9B65D8CD9165FD7503FD7404FD7505FD7406117744217E65C3E458B4
:19657E00FD6E05FD6606110800197E23B62B20E1C3AA58FD7E0732A0C697
:08659700CD9B54C9AF32A1C332
:0B659F00CDA240CDBA6230253A9EC369
:0465AA004F3A9FC302
:0365AE003250C1A7
:0B65B1004 7CB43280BB93EFF32A1C3CB
:0865BC00280978180 63A9DC376
:0365C4003250C191
:0365C70032A0C639
:0965CA00180ACDAA40D83AA0C677
:0365D3003250C182
:2065D600FD7707FD360004FD360800B7C9111466F7112566F7CD154ACD7E40FD7E074F3C5F
:0565F60020123AA4C3CD
:0E65FB00B72804112C66F7113466F73A9FC3D7
:206609004F113766F779C6307723C90D0D0D4C4320434F4E444954494F4E538D0D554E4955
:206629005420A0414C5445524544A05255CE2046494C4520A00D0D455854454E4445C4E557
:20664900CD9165119201197EE13C2004113E66F7115E66F7C90D0D202054494D45202020C8
:206669002020254120202020202542202020202543202020202046C4F578DE5CD91654F
:20668900FD4608CBB8110800ED521910FDE5DDE1E1CD9340CD5B67CD5667CD2B67C03AA16E
:0166A900C32D
:1066AA003C2803CD9340DD5E00DD5601ED5352C117
:1066BA00FDCB08FEC9FD7E07CD1C6720623A50C19A
:0A66CA003CFE0A2001AF4F3250C120
:0366D4003A9EC328
:0E66D700B920020EFF79CD1C6720473AA1C3FF

```
:1666E5003C280BCD2B672026FD3608001824CD2B6728312A52C11F
:2066FB00DD5E08DD5609ED52FD360802200ADD7E10DDB61128181804FD360801FD71073707
:04671B00C932A0C619
:20671F00CD9B54E5DDE1CD3E58C9B7C9DD7E08DDB609C90E00CD8546D27A40C90E02CD852A
:20673F0046D27640C90E03CD8546D27640C90E04CD8546D27A40C90E01C38546CD3267CDDA
:20675F003B67CD4467C34D67E5CD9165E5DDE1E1CD9340CD9340118E67F7CD8567CD9340C7
:20677F00CD9340C39340CD0F09CDA547C3A2674D41582E2050524553532E204C494D4954CC
:20679F00203DA0113F681803113B68F7C9CDA540D2C641D73EFFFD360004FD770721C267FB
:2067BF00C3FD5811CA6721DE67182A11D167F7C3E7650D0D0D4C43205354415455538D1111
:2067DF00486621E667180E11F76721EE671806111B68215765C3E458CD9340CDC846CDCDD0
:1C67FF0014CD7A40CD2E47CD7640CD3747CD7640CD4047CD7A40CD0947C39340C2
:08681B00112668F7ED5B0AC0CD
:20682300C388670D43555252454E5420205052455353555245203DA0204241D2205053C9BC
:2068430059CDA240FDE5C50E05CD2A6EC1FDE13006111D00C3CE41CDBA62DACB41CDAA40B3
:04686300D83AA0C6B9
:03686700329DC39C
:06686A00CD9B542297C3F0
:036870002299C3A7
:07687300FD3600053AA0C646
:07687A00FD7707AF3247C1B3
:20688100FD360800218B68C3FD5811946821A468C3E458119B68F7C3F1650D0D534F4C56D5
:0768A100454ED4DD2A97C328
:2068A800DD7E02DDB6032013DD7E08DDB609200BDD6E04DD6605CDAD69283411CB6821DD68
:2068C80068184B11D068F7C9050D45524153452046494C45BFCD436DC8FE0221D66A28127B
:1E68E800FE04280EFE052803D718D0D7CD9D5E210069114866C3E45821000022A0C6DD
:15690600C3536B11196A211E69CD5E6DFDCB08DE3E013247C100
:1E691B00C3E458CD436DC8FE02280BFE032833FE07202FC3BC6BFDCB086EDD2A99C3AC
:0B693900DD6EFCDD66FD28032AA4C60D
:20694400CD6869CDAA6911646ACA4D6ACD3C6DFDCB08D621C869C3E458CDDD623022210960
:0769640069C3596D22A4C6AE
:05696B003E04325DC393
:18697000FDCB086E2005CDD2531803CD6953D7FDCB087EC9ED5BA4C676
:0A698800D5CD6869280AE122A4C6F3
:12699200210969C3496DD1CDAA69201621000022A6C651
:0969A400115E6AC34D6A2AA4C603
:2069AD0011E803AFED52C911C069CD3C6D21C869C3E458CD346D0613C3536DCD436DC8FEC9
:0F69CD0002280FFE032826FE072022AF325FC3E9
:0B69DC00C3BC6BFDCB086EDD2A99C325
:0B69E700DD6EFDDD66FF28032AA6C659
:2069F200CD206A11706A1853CDDD62D2356A21066AC3596DCD3C6DCD5E6DFDCB08D6111963
:116A12006A21C869C3E458FDCB08BEC3086C22A6C665
:056A23003E0D325DC3D1
:116A2800CDD253FDCB08CED7FDCB087EC9ED5BA6C62B
:0A6A3900D5CD206A280AE122A6C686
:206A4300210969C3496DD1116A6ACD3C6DFDCB0896FDCB08CE21766AC3E458CD346DC3289E
:206A63006CCD346DC3256CCD346DC3356CCD346DC8FE022807FE07CABC6BDA
:206A8300182611476C21D26AC3E458CD3C6DFDCB08BE119E6A21766AC3E458CD346DCD5EDF
:1B6AA3006DFDCB08CEC30E6C3E02CDDF623009CDC641218E6AC3496D22A2C619
:056ABE003E02325DC341
:206AC300CD6953FDCB087E2806218E6AC3496DFDCB08AECD3C6DFDCB08E611086C21E66A7C
:206AE300C3E458CD436DC8FE022830FE07200218DEFE062031FDCB086E2830CD136BFDCBDC
:146B030008AE2805CD535418CACD5354D7C30969ED5B99C321
:036B17002A97C3F7
:1F6B1A00AFED52C9FDCB086ECA4E6CD7C30969CDDD62300621D66AC3596DD5E522A0C669
:0D6B3900CDCD55E1D1CAD26A3E01325DC317
:0D6B4600EB0E00CDB154EB3824DD2299C3D5
:206B5300FDCB08EECDF36BCDEB6BD7CD5E6DCD136B11086C210969CAE45821D66AC3E458DE
:036B730022A0C697
:056B76003E01325DC389
:1D6B7B00FDCB086E2812CDF36BCD6953FDCB087E281B21576BC3496D3E01325FC351
:206B9800CDD253D7FDCB087E280621D66AC3496DCD3C6D11B46B211E69C3E458CD346D06FD
:1E6BB8000CC3536DFDCB086E2005CD53541806CD5354CDD06BC3D26ACDEB6B3AA3C6FA
:096BD600FEFF20093E01325FC3FD
:096BDF003E0D18023E0F325DC3A9
:066BE800C3D25321A0C638
:036BEE001148C18A
:056BF100180C2148C151
:056BF600180321A0C6F8
:046BFB00ED5B99C3F2
```

```
:206BFF0006081A77231310FAC9CD346D360D230603CD536DFDCB0866C0CD3267060CCD53D6
:206C1F006DFDCB085EC0CD3B670613CD536DFDCB0856C0CD4467061ACD536DCD4D67062132
:0C6C3F00CD536DFDCB084EC0DD2A99C37B
:176C4B00C35667CD3C6D115A6C21846CC3E458116A6CF7DD2A97C316
:206C6200CD8567117F6CF7C9050D4D41582E20505245535320A8202920CC
:206C82003DA0CD436DC8FE02CAAD6CFE0728BDAFCDDF623006214E6CC3596DAFCD83632228
:026CA200AAC680
:036CA400215DC3AC
:206CA700CBEECD3C57EFCD3C6D11B96C21DD6CC3E45811C56CF7CD714711D66CF7C9050DCD
:206CC7000D564F4C554D452044454C415920A8204D4C29203DA0CD436DC8FE02281AFE0706
:106CE70028C4CDDD62D2F46C21AD6C186522AEC626
:036CF700215EC358
:206CFA00CBC6CD5857D7EF110A6D212E6DC3E45811116DF7C393400D0D454E44204F462082
:206D1A00534F4C56454E542046494C45204449414C4F478DCD6259C3AA58360523DD21A048
:016D3A00C692
:066D3B00C93E013247C110
:056D4600D7C93A47C16B
:206D4600FE01C9D7C3FD58FD7E00FE05C93610237023C9CDC64118EBFD7E08E6E0FD7708CE
:0E6D6600C9CDA540DACB41CDAA40D83AA0C68F
:146D7400FE05CA7C6DC3C64111826DC3E458CDCC6121D6C5D6
:206D880020073E0ACD60461804119B6DF7CD7147C3934050562003DA000FDE5CD286EFDE1FC
:096DA800D8DD21026EAF3261C397
:0C6DB100EF11FFFFCDC362D8ED5BA0C660
:206DBD00DD6E00DD23DD6600DD237CB5C8AFED522806DD23DD2318E8D7FD360006FDE5FD24
:036DDD0021ADC322
:1D6DE0000608FD7E00FE03CC6259113000FD1910F1FDE1DD6E00DD6601ED5B47C36E
:206DFD000664C3D847C8003F6EC900886ECA00936FCB00A36FCC000770CD005D71CE006938
:136E1D0071CF008771D000497200000E060608FD21ADC3EF
:146E3000FD7E00B937C8113000FD1910F3B7C93E01329BC075
:206E44000601ED5B91010121000CD746EB8200E3A9001B82804041918F00666180D581600C4
:206E64000604216C6EC3C96F0667CD0459C3D372C5D5E5AF191B2B86CE00477AB37820F58D
:096E8400E1D1C1C93E02329BC0FC
:206E8D00CDFF5FCD8503F3210849015F0AEDB33E37D3BFC3D76EAF7C1F477D1F4F09EBD99E
:206EAD00B78B1D908380B370801000010FE0D20FBD9D9FD23FD232D1810FD08A300DF0E1B
:126ECD00230AD6071508390E080B1101007AD92100C0EC
:1B6EDF00545D01FF007713EDB06BED4B930105D97BD977EDB0D9AF082100C0D2
:156EFA00ED4B93017A08BD283308EDA1207BEAFF6ED92100C0DB
:116F0F00ED4B93010B09EB6B622BEDB8D9082100C047
:206F2000723C20D2CB02CB137BAA20AE7AB7200D11FEFFC3DA6E087BEDA17A18C92100C04F
:036F40001100C07D
:206F4300ED4B930136FFAFED522005AF626B181AAFED5A3EFF12BE2027AF123DBE202136EF
:1E6F63000012AFBE201A12BE2016EBEDA1EBEA476F23EBAFED52EB20C43E0132AAC3A4
:076F810018053E0232AAC30D
:036F880021D1D83C
:056F8B00F9AF32A9C3BB
:086F9000C331483E03329BC0EF
:036F98002154C3BE
:0D6F9B005E16003600C3C46F3E04329BC07A
:036FA8003A8EC05E
:206FAB00CDB16FC3C46F5F1600016400210000CD9601016000CD0302C9060321D972C5D579
:206FCB0011DD6FCDE458D1C1FD700FFD730DFD720EC9FD5E0DFD560E060078CD604678FD40
:206FEB00BE0FCC1440CD8F400478FE0520EC3E08CD0170C39340CD6046C38F403E05329B43
:01700B00C0C4
:05700C003EFF329DC0B3
:09701100211770C3FD583A9BC021
:08701A00FE05C2C1723A9DC0DF
:0B702200B7C021D972C313713A9BC0A4
:06702D00FE05C03A9DC003
:067033003C20223A52C08D
:0C703900473A4C01B8C03A4A01329DC0F1
:0670450021FF7F229EC026
:03704B0022A2C0BE
:06704E0021000022A0C099
:0370540022A4C0B3
:04705700C93A7BC0F7
:05705B00B7C83A52C065
:12706000473A4B01B828523A4C01B8C0CDBE70219DC0A7
:0870720035C0CDE77022A6C075
:05707A00EBD521B5C2B9
```

```
:03707F00229DC18E
:1C708200CD8E2221203A011800EDB0E1EBCD1740060CCD8840E5CDEC7022A8C015
:0D709E00EBE1CD1740CD3820C9DD219EC0AB
:0470AB00FD21A0C063
:0570AF00C9DD21A2C0B3
:0470B400FD21A4C056
:0D70B800C9CDA7701803CDB070ED5B15C0F9
:2070C500DD6E00DD6601AFED523806DD7300DD7201FD6E00FD6601AFED52D0FD7300FD72E4
:2070E50001C9CDA7701803CDB070DD5E00DD5601FD6E00FD6601AFED52EB01E803210000B1
:20710500CD9601FD4E00FD4601CD0302EBC9111971C3E458AFCD01703E02114571CDA046B0
:207125003E03115071CDA0463E04114A71CDA0463E01115671CDA0463E08CD0170C39340DF
:0F714500110100180311020000C31440ED5BA8C034
:067154001804ED5BA6C06B
:08715A00C317403E06329BC042
:04716200ED5B4CC0D5
:08716600C3C46F3E07329BC059
:03716E003A6AC0BA
:1B717100E604280ADBFAE6012804066718020666CD0459C3D3723E08329BC007
:04718C00AF32B2C0AC
:0C719000CDFF5F210000CD3612216AC047
:10719C007EE67FF644D3F977DD211E72DD22ABC08B
:1971AC00DD5E00214D0156DBFAE63EBB2811CD27721520F33E0132AAC074
:0A71C500210272C3DC72AF32AAC0CF
:0971CF0021D571C3FD583A9BC0A3
:0B71D800FE082026CD2772DD2AABC088
:1071E300DD23DD7E00B72004DD211E72DD22ABC06E
:0E71F300DD5E00DBFAE63EBBC83E0132AAC0FC
:04720100C9216AC075
:0B7205007EE603D3F97706663AAAC0C4
:1A721000B728020667CD045921AA58C3D8470C0E0616121A181C003A6AC0ED
:20722A00F680D3F9E67FD3F9D52E08ED4B4E01CD2E12E5210000CD3612E12D20EED1C93E23
:04724A0009329BC0AA
:0B724E00CDFF5FCD85033E103244C130
:0B725900216172CDFD5818083A9BC05F
:08726400FE09C2C1722144C100
:14726C005EAF7E17B72804FE8020023E1077C37D723A6AC00E
:0D728000E60FB3E67FD3F93A77013243C140
:14728D00C957CD2E12CD2E12CB7A20057AF68018E73A6AC0F6
:0C72A100E60FD3F9C9CD286ED03A9BC08F
:0B72AD00B7C8180ACD286ED03A9BC06D
:0C72B800FE05C0210000C3DC723A61C377
:1E72C400B7200621AA58C36B6121AA58C3FD5821D972C3D84721AA58C5E5AF329BC08B
:0372E200329DC01A
:0372E50032AAC307
:0472E800ED5B47C350
:0872EC000665CDD847E1C1C9D8
:00000001FF
```

What is claimed is:

1. An apparatus for causing controlled flow of a solvent composition through a liquid chromatography column comprising:

means for pumping a solvent composition comprised of one or more solvents through said column at a constant pressure determined by a pressure control signal including a dual piston pump means for pumping said solvent composition at a pressure determined by said pressure control signal where said dual pistons each have their own cylinder and are driven by the same rotating shaft and an associated drive mechanism such that said pistons have an associated overlap interval in the rotation of said rotating shaft during which both pistons are pushing said solvent composition out their respective cylinders, and where each piston has an intake interval in the rotation of said rotating shaft during which said solvent composition is being drawn by each respective piston into the associated cylinder, said intake interval including a linear interval defined by a constant piston velocity, and further including control means including transducer means for detecting data indicating the actual pressure at the output of said means for pumping, said control means for comparing the actual pressure detected by said transducer means to the desired pressure as determined by said pressure control signal and for controlling the speed of rotation of said rotating shaft during intervals including said overlap interval such that the actual pressure at the output of said means for pumping equals the desired pressure; and computer means for for receiving data defining the desired flow rate and for determining a correction factor determined by the compressibility of the solvent composition by computing the ratio of the duration of a first interval during which said rotating shaft is moving said pistons through said overlap interval for the current solvent composition and the current actual constant pressure to the duration of a second interval during which said rotating shaft is moving said pistons through said overlap interval for incompressible solvent pumped at a constant pressure, each said first and second intervals being normalized to the time it takes said rotating shaft to rotate through a predetermined angle during which the corresponding one of said pistons moves during the corresponding one of said respective linear intervals, where said predetermined angle is equal to the angle through which said rotating shaft moves while said pistons are in said overlap interval, and said computer means for subtracting one from each said normalized first and second interval before computing said ratio and for multiplying said ratio times a volume factor equal to the amount of volume displaced by one of said pistons during said overlap interval to derive a product and for subtracting said product from said volume factor to derive said correction factor, and for updating said pressure control signal by multiplying the value of the old pressure control signal times the quantity equal to the correction factor plus 1.

2. The apparatus of claim 1 further comprising a plurality of valve means each said valve means being coupled to said computer means by a mixture control signal controlling the amount of time said valve means is open, said valve means for coupling a plurality of solvents to the solvent composition input of said means for pumping, said computer means for receiving data defining how much of each said solvent is to be present in the solvent composition at the output of said means for pumping and for generating each said mixture control signal so that each said valve means is opened during a separate, appropriate interval during said linear interval of one of said pistons where said appropriate interval in recalculated and the corresponding one of said mixture control signals is updated on each cycle of said rotating shaft by multiplying the old interval established by the corresponding one of said mixture control signals for each solvent times a quantity equal to one minus the correction factor.

3. The apparatus of claim 2 wherein said computer means recalculates said correction factor on each cycle of said rotating shaft and updates said pressure control signal on each said cycle.

4. An apparatus for causing controlled flow of a solvent composition through a liquid chromatography column at a constant flow rate comprising:

pump means having an input port and having an output port coupled to the solvent input of said column for pumping a solvent composition comprised of one or more solvents from said input port through said column at a flow rate determined by a control signal, said pump means comprising two pistons driven by a rotating shaft which pump said solvent composition out from said output port on different cycles but including an overlap interval during which both said pistons are simultaneously pumping and a linear interval during which at least one of said pistons is traveling at a constant velocity in drawing in said solvent composition, and further comprising pressure sensor means for sensing the actual pressure at said output port and generating an actual pressure signal and control means coupled to receive said actual pressure signal for altering the speed of said pump means to maintain the flow rate defined by said control signal; and one or more electrically controllable valve means each said valve means coupling a source of each solvent in said solvent composition to said input port of said pump means, each said valve means having a control input for receiving a mixture control signal, each said valve means for controlling the amount of each solvent in said solvent composition in accordance with said mixture control signal;

computer means coupled to said pump means and to said valve means for maintaining the desired flow rate and the desired solvent composition over changing operating pressures and changing solvent compositions and despite changes in other operating conditions by determining the compressibility of the solvent composition by determining a plurality of times and calculating a correction factor for compressibility using the formula, $$CF = Z - [(Z/((T_{df}/T_{lf}) - 1))((T_{mdf}/T_{mlf}) - 1)]$$

where, $CF$ = the correction factor to be used to account for compressibility of the solvent at the solvent composition, operating pressure at the output of said pump means and other operating conditions existing for the current revolution of said rotating shaft, $Z$ = a constant equal to the percentage of each piston's pump stroke volume traversed during said overlap interval, $T_{lf}$ = the time for the rotating shaft to rotate through an angle during said linear interval said angle being equal to the angle said rotating shaft rotated through during said overlap interval under the same operating conditions of pressure and flow rate and incompressibility of solvent as were used to determine $T_{df}$, $T_{mdf}$ = measured time for the rotating shaft to rotate through the angle defining said overlap interval with the current compressible solvent composition at the current constant flow rate, and $T_{mlf}$ = measured time for the rotating shaft to rotate through the same angle in said linear interval as used to determine $T_{lf}$ but with the same flow rate, solvent composition and operating pressure used to measure $T_{mdf}$, and for generating said control signal and for updating said control signal from time to time using said correction factor by multiplying the value of the old control signal times the quantity (CF+1) to establish the desired flow rate and for causing said electrically controllable valve means to be opened for the amount of time necessary for input of each solvent component to cause the final solvent composition to be substantially as desired over all conditions of compressibility by calculating the number of degrees of rotation of said rotating shaft during said linear interval each said valve means is to be opened to obtain the desired amount of intake of each corresponding one of said solvents and for generating one or more of said mixture signals to cause each said valve means to be opened separately for the calculated interval during said linear interval and for, from time to time, updating said mixture signal for each said valve means to take into account the effect of compressibility of said solvent by multiplying the value of each mixture signal by the quantity (1−CF).

5. An apparatus comprising:

means for pumping solvent coposition of one or more solvents through a liquid chromatography column at a constant flow rate including control means for controlling said means for pumping to obtain a flow rate determined by a control signal and for controlling said means for pumping during an overlap interval during which the flow rate will increase unless the means for pumping is slowed down by said control means and for controlling said means for pumping during a linear interval so that said means for pumping is driven at a constant velocity to obtain the desired flow rate; and means for gating the solvent components into said means for pumping to make up said solvent composition; and means coupled to said control means for determining the compressibility of the solvent composition being pumped through said column by comparing the time it takes said means for pumping to traverse said overlap interval with the current solvent composition to the time it takes said means for pumping to traverse said overlap interval with an incompressible solvent at the same flow rate and for generating said control signal in such a manner as to obtain the desired constant flow rate over changing conditions of compressibility of the current solvent composition and for controlling the means for gating so that the desired solvent composition is maintained over changing conditions of compressibility and wherein said means for determining the compressibility stores therein a time TDF for travel of a first piston through said overlap region of its cycle with an incompressible solvent at low pressure and constant flow rate and a time $T_{LF}$ for travel through a portion of the constant velocity portion of its travel equal to the angle of said overlap region under the same conditions under which TDF was determined, said times being stored as constants for each flow rate of solvent through the column that the user might request and wherein the means for compressibility measures the time $T_{MDF}$ required for the first piston to travel through its overlap region at the desired constant flow rate and the time $T_{MLF}$ required for the first piston to travel through the same portion of its constant velocity portion of travel as used to determine $T_{LF}$ at a constant flow rate and under the same conditions under which $T_{MDF}$ was measured and wherein the means for determining compressibility calculates a correction factor for compressibility by the following expression:

$$CF = Z - \frac{Z[T_{MDF}/T_{MLF} - 1]}{[T_{DF}/T_{LF} - 1]}$$

where Z equals the volume displaced as said first piston traverses the overlap region.

6. The apparatus of claim 5 wherein said means for pumping is a dual piston pump wherein each piston is driven by a cam and wherein a first piston pumps solvent from an input through a check valve into the cylinder housing a second piston and wherein said second piston pumps solvent out from its cylinder through an output and wherein said cam contours are such that there is an overlap portion of each cycle wherein both said pistons are pumping simultaneously.

7. The apparatus of claim 5 wherein the means for gating comprises a solenoid operated valve which couples a source of each solvent in the composition to said means for pumping wherein the control signal input of each solenoid operated valve is coupled to said means for determining compressibility.

8. The apparatus of claim 7 wherein the means for determining compressibility prompts the user for data regarding the desired solvent composition and uses the percentage of the minor solvents in the composition times a constant to determine the number of steps to open each solenoid operated valve during the input stroke of said first piston and wherein said constant is multiplied by one minus said correction factor to determine the actual number of steps to open each solenoid valve controlling a minor solvent.

9. The apparatus of claim 8 wherein the first piston has a constant velocity portion of its input stroke and each minor solvent solenoid operated valve is opened separately during a portion of said linear portion of said input stroke and wherein said means for determining compressibility also is coupled to said means for pumping to control its speed by calculating a target pressure control signal based upon a user input regarding the desired flow rate and for correcting said target pressure control signal based upon the compressibility of said solvent composition.

* * * * *